US006492179B1

(12) United States Patent
Bar-Or et al.

(10) Patent No.: US 6,492,179 B1
(45) Date of Patent: *Dec. 10, 2002

(54) TEST FOR RAPID EVALUATION OF ISCHEMIC STATES AND KIT

(75) Inventors: David Bar-Or, Englewood; Edward Lau, Boulder; James V. Winkler, Denver, all of CO (US)

(73) Assignee: Ischemia Techologies, Inc., Arvada, CO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 31 days.

(21) Appl. No.: 09/165,581

(22) Filed: Oct. 2, 1998

(51) Int. Cl.$^7$ ......................... G01N 33/20; G01N 33/48; G01N 33/00; G01N 33/53; C12Q 1/00

(52) U.S. Cl. ............................. 436/74; 436/63; 436/73; 436/74; 436/86; 436/87; 436/88; 436/171; 436/903; 436/904; 436/518; 435/4; 435/7.1; 422/55; 422/66; 422/82.05; 422/82.09; 422/56; 422/58

(58) Field of Search .......................... 422/55.61, 82.05, 422/82.09, 2, 56, 58; 436/86, 63, 903, 74, 73, 904, 518, 87, 171, 88; 435/4, 7.1, 709, 810, 26, 77, 16; 252/183.11, 183.13

(56) References Cited

U.S. PATENT DOCUMENTS

| | | | |
|---|---|---|---|
| 3,955,926 A | | 5/1976 | Fischer |
| 4,379,848 A | | 4/1983 | Yeaw |
| 4,434,234 A | | 2/1984 | Adams et al. |
| 4,468,466 A | | 8/1984 | Morrissey |
| 4,486,282 A | | 12/1984 | Bier |
| 4,492,753 A | | 1/1985 | Shell et al. |
| 4,713,327 A | | 12/1987 | Findlay et al. |
| 4,786,605 A | | 11/1988 | Mauck et al. |
| 5,227,307 A | * | 7/1993 | Bar-Or et al. |
| 5,290,519 A | * | 3/1994 | Bar-Or et al. |
| 5,604,105 A | | 2/1997 | Jackowski |
| 5,710,008 A | | 1/1998 | Jackowski |

FOREIGN PATENT DOCUMENTS

WO     WO00/20454     4/2000

OTHER PUBLICATIONS

Kadota, MD, et al., "Decreased Sulfhydryl Groups of Serum Albumin in Coronary Artery Disease," Japanese Circulation Journal, vol. 55, pp. 937–941, (Oct. 19, 1991).*
Braughler, "Calcium and Lipid Peroxidation," From Central Nervous System Diseases Research Unit, p. 99 (1987), The Upjohn Company, Kalamazoo, Michigan.*
Witko–Sarsat, "Advanced Oxidation Protein Products as a Novel Marker of Oxidative Stress in Uremia," Kidney International vol. 49, pp. 1304–1313 (1996), International Society of Nephrology, Paris, France.*
Davies, "Protein Damage and Degradation by Oxygen Radicals," The Journal of Biological Chemistry vol. 262, No. 20, Issue of Jul. 15, pp. 9895–9901; 9002–9907; 9914–9920, (1987), University of Southern California, Los Angeles, California.*
Keller, "Immunochemical Detection of Oxidized Proteins," Chem. Res. Toxicol vol. 6, No. 4, pp. 430–433 (1993), Occupational and Environmental Health Program and Division of Toxicology, University of Arkansas for Medical Sciences, Little Rock, Arkansas.*
Halliwell, "Oxygen Radicals and Tissue Injury," Proceedings of a Brook Lodge Symposium pp. 100–104 (Apr. 1987), Augusta, Michigan.*
Davies, "Oxygen Radicals Stimulate Intracellular Proteolysis and Lipid Peroxidation by Independent Mechanisms in Erythrocytes," From the Department of Physiology and Biophysics, Harvard Medical School, vol. 262, No. 17, Issue of Jun. 15, pp. 8220–8225, (1987), Boston, Massachusetts.*
"DNA Damage Linked to Risk of Breast Cancer Spread," found at http://www.pslgroup.com/dg/6c2e.htm.*
Ishimoto, "Role of Oxygen–Derived Free Radicals in Fetal Growth Reardation Induced by Ischemia–Reperfusion in Rats," found at http://oac3.hsc.uth.tmc.edu/apstracts/1996/heart/September/37lh.html, p. 1 (Sep. 1996), published in APStracts on Sep. 19, 1996.*
Hisashi, "Atp–sensitive k+ channels in Pancreatic, Cardiac, and Vascular Smooth Muscle Cells," found at http://oac3.hsc.uth.tmc.edu/apstracts/1997/cell/October/

(List continued on next page.)

*Primary Examiner*—Nita Minnifield
*Assistant Examiner*—Padma Baskar
(74) *Attorney, Agent, or Firm*—Swanson & Bratschun, LLC

(57) ABSTRACT

The present invention relates to a rapid method for the detection of ischemic states and to a kit for use in such a method. Provided for is a rapid method of testing for the existence of and quantifying ischemia based upon method of detecting and quantifying the existence of an alteration of the serum protein albumin which occurs following an ischemic event; methods for detecting and quantifying this alteration include evaluating and quantifying the cobalt binding capacity of circulating blood, analysis and measurement of the ability of serum albumin to bind exogenous cobalt, detection and measurement of the presence of copper in a purified albumin sample and use of an immunological assay sepcific to the altered form of serum albumin which occurs following an ischemic event. Also taught by the present invention is the use of the compound Asp-Ala-His-Lys-R, wherein R is any chemical group capable of being detected when bound to any compound capable of binding to the N-terminus of naturally occurring human albumin (including no additional chemical group), for detection and quantification of an ischemic event.

19 Claims, 4 Drawing Sheets

OTHER PUBLICATIONS 291C.html, p. 1 (Oct. 1997), published in APStracts on Oct. 7, 1997.*

Cobbe, S.M., et al., "The Time of Onset and Severity of Acidosis in Myocardial Ischemia," J. of Mol. Cell. Card., Academic Press Inc. Limited (London), pp. 745–760, (Jan. 12, 1980).*

Reimer, K.A., MD, Ph.D., et al, "The Wavefront Phenomenon of Ischemic Cell Death 1. Myocardial Infarct Size vs Duration of Coronary Occlusion in Dogs," Circulation, Department of Pathology, Duke University Medical Center (Durham, North Carolina), pp. 786–793, (Jan. 12, 1977).*

Reimer, K.A., MD, Ph.D., et al., "Myocardial Ischemia, Hypoxia, and Infarction," The Heart and Cardiovascular System: Scientific Foundations, Raven (New York), pp. 1875–1953, (Jan. 12, 1992).*

Ishikawa, Y., et al., "Reversible Myocardial Ischemic Injury is Not Associated with Increased Creatine Kinase Activity in Plasma," Clin. Chem., Department of Medicine, University of Kobe (Kobe, Japan), vol. 43 (No. 3), pp. 467–475, (Jan. 12, 1997).*

Roberts, R., MD, et al., "Rapid MB CK Subform Assay and the Early Diagnosis of Myocardial Infarction," Clin. Lab. Med., Departments of Medicine and Cell Biology, Section of Cardiology and the Bugher Foundation Center for Molecular Biology, Baylor College of Medicine (Houston, Texas), vol. 17 (No. 4), pp. 669–683, (Dec. 12, 1997).*

Gobel, E.J.A.M, et al., "Long–term Follow–up After Early Intervention with Intravenous Diltiazem or Intravenous Nitroglycerin for Unstable Angina Pectoris," Eur. Heart J., Department of Cardiology, University Hospital Groningen (Groningen, The Netherlands), pp. 1208–1213, (Feb. 12, 1998).*

Pepine, Carl J., MD, et al., "Effects of Treatment on Outcome in Mildly Symptomatic Patients with Ischemia During Daily Life The Atenolol Silent Ischemia Study (ASIST)," Circulation, American Heart Association Inc. (USA), pp. 762–768, (Jan. 12, 1994).*

Hedges, Jerris R., MD, et al., "Prospective Assessment of Presenting Serum Markers for Cardiac Risk Stratification," Acad. Emerg. Med., Hanley & Belfus, Inc. (USA), vol. 3, pp. 27–33, (1996).*

Laussac, Jean–Pierre, et al., "Characterization of the Copper(II)—and Nickel(II)—Transport Site of Human Serum Albumin, Studies of Cooper (II) and Nickel(II) Binding to Peptide 1–24 of Human Serum Albumin by 13C and 1H NMR Spectroscopy," Biochem, American Chemical Society (USA), vol. 23, pp. 2832–2838, (Jan. 12, 1984).*

Predki, Paul F., et al., "Further Characterization of the N–terminal Cooper(II)—and Nickel(II)—Binding Motif of Proteins," Biochem. J., Department of Biochemistry Research, The Hospital for Sick Children (Toronto, Ontario, Canada), vol. 287, pp. 211–215, (Jan. 12, 1992).*

Masuoka, James, et al., "Intrinsic Stoichiometric Equilibrium Constants for the Binding of Zinc(II) and Copper(II) to the High Affinity Site of Serum Albumin," J. Biol. Chem., The American Society for Biochemistry and Molecular Biology, Inc. (USA), vol. 268, pp. 21533–21537, (Jan. 12, 1993).*

Sadler, P.J., et al., "Involvement of a Lysine Residue in the N–terminal Ni2+ and Cu2+ Binding Site of Serum Albumins. Comparison with Co2+, Cd2+ and A13+," Eur. J. Biochem., found at http://search19.proxy.aol.com:8000/post–query/MedLine/hrs1994/23450?albumin+n+terminal (USA), pp. 193–200, (Jan. 12, 1994).*

Chan, Bernard, et al., "Site–specific N–terminal Auto–degradation of Human Serum Albumin," Eur. J. Biochem., Delta Biotechnology Limited (Nottingham, England), vol. 227, pp. 524–528, (Jan. 12, 1995).*

McCord, J., Ph.D., "Oxygen–derived Free Radicals in Post Ischemic Tissue Injury," NEJM, Department of Biochemistry, College of Medicine, University of South Alabama (Mobile, Alabama), vol. 312, pp. 159–163, (Jan. 12, 1985).*

Afanas'ev, Superoxide Ion: Chemistry and Biological Implications, vol. II, Oxygen Radicals in Biology, CRC Press, Boca Raton, FL pp. 138 and 187.*

Boehringer Kit, Catalog No. 15946, p. 375.*

Dolovich et al. (1984) British Journal of Industrial Medicine 41:51.*

Fleming and Nixon (1986) Analytical Biochemistry 154:691.*

Genest, Jr. et al. (1990) JACC 16:1114.*

Glutathione, Interconversion of Glutathione and Glutathione Disulfide, pp. 733–739.*

Karck et al. (1992) The Journal of Heart and Lung Transplantation 11:979.*

Mangano et al. (1990) The New England Journal of Medicine 323:1781.*

Metal–Binding Groups of Proteins, A. Evidence for Specific Donor Atoms, Chapter IV, pp. 61–99.*

Nieborer et al. (1984) British Journal of Industrial Medicine 41:56.*

Odeh (1991) New England Journal of Medicine 324:1417.*

Shirakawa et al. (1992) Clinical and Experimental Allergy 22:213.*

Shirakawa et al. (1990) Thorax 45:267.*

Shirakawa et al. (1988) Clinical Allergy 18:451.*

Toxicity and Physicochemical Properties of Metals, Coordination and Chelation, Chapter 4, pp. 115–122.*

Veien et al. (1979) Contact Dermatitis 5:378.*

Venugopal and Luckey, Metal Toxicity in Mammals, vol. 2, Chapter 8, pp. 280–289, Plenum Press, New York and London.*

Yoon et al. (1989) Journal of Surgical Research 46:163.*

Kadota, MD, et al., "Decreased Sulfhydryl Groups of Serum Albumin in Coronary Artery Disease," Japanese Circulation Journal, vol. 55, pp. 937–941, (Oct. 19, 1991).

Braughler, "Calcium and Lipid Peroxidation," From Central Nervous System Disease Research Unit, p. 99 (1987), The Upjohn Company, Kalamazoo, Michigan.

Witko–Sarsat, "Advanced Oxidation Protein Products as a Novel Marker of Oxidative Stress in Uremia," Kidney International vol. 49, pp. 1304–1313 (1996), International Society of Nephrology, Paris, France.

Davies, "Protein Damage and Degradation by Oxygen Radicals," The Journal of Biological Chemistry vol. 262, No. 20, Issue of Jul. 15, pp. 9895–9901; 9902–9907; 9914–9920, (1987), University of Southern California, Los Angeles, California.

Keller, "Immunochemical Detection of Oxidized Proteins," Chem. Res. Toxicol vol. 6, No. 4, pp. 430–433 (1993), Occupational and Environmental Health Program and Division of Toxicology, University of Arkansas for Medical Sciences, Little Rock, Arkansas.

Halliwell, "Oxygen Radicals and Tissue Injury," Proceedings of a Brook Lodge Symposium pp. 100–104 (Apr. 1987), Augusta, Michigan.

Davies, "Oxygen Radicals Stimulate Intracellular Proteolysis and Lipid Peroxidation by Independent Mechanisms in Erythrocytes," From the Department of Physiology and Biophysics, Harvard Medical School, vol. 262, No. 17, Issue of Jun. 15, pp. 8220–8225, (1987), Boston, Massachusetts.

"DNA Damage Linked to Risk of Breast Cancer Spread," found at http://www.pslgroup.com/dg/6c2e.htm.

Ishimoto, "Role of Oxygen–Derived Free Radicals in Fetal Growth Reardation Induced by Ischemia–Reperfusion in Rats," found at http://oac3.hsc.tmc.edu/apstracts/1996/heart/September/37lh.html, p. 1 (Sep. 1996), published in APStracts on Sep. 19, 1996.

Hisashi, "Atp–sensitive k+ channels in Pancreatic, Cardiac, and Vascular Smooth Muscle Cells,"found at http://oac3.hsc.uth.tmc.edu.edu/apstracts/1997/cell/October/291C.html, p. 1 (Oct. 1997), published in APStracts on Oct. 7, 1997.

Cobbe, S.M., et al, "The Time of Onset and Severity of Acidosis in Myocardial Ischemia," J. of Mol. Cell. Card., Academic Press Inc. Limited (London), pp. 745–760, (Jan. 12, 1980).

Reimer, K.A., MD, PH.D., et al, "The Wavefront Phenomenon of Ischemic Cell Death 1. Myocardial Infarct Size vs Duration of Coronary Occulsion in Dogs," Circulation, Department of Pathology, Duke University Medical Center (Durham, North Carolina), pp. 786–793, (Jan. 12, 1977).

Reimer, K.A., MD PH.D., et al., "Myocardial Ischemia, Hypoxia, and Infarcation," The Heart and Cardiovascular System: Scientific Foundations, Raven (New York), pp. 1875–1953, (Jan. 12, 1992).

Ishikawa, Y. et al, "Reversible Myocardial Ischemic Injury is Not Associated with Increased Creatine Kinase Activity in Plasma," Clin. Chem., Department of Medicine, University of Kobe (Kobe, Japan), vol. 43 (No. 3), pp. 467–475, (Jan. 12, 1997).

Roberts, R., MD, et al., "Rapid MB CK Subform Assay and the Early Diagnosis of Myocardial Infarcation," Clin. Lab. Med., Departments of Medicine and Cell Biology, Section of Cardiology and the Bugher Foundation Center for Molecular Biology, Baylor College of Medicine (Houston, Texas), vol. 17 (No. 4), pp. 669–683, (Dec. 12, 1997).

Gobel, E.J.A.M, et al., "Long–term Follow–up After Early Intervention with Intravenous Diltiazem or Intravenous Nitroglycerin for Unstable Angina Pectoris," Eur. Heart J., Department of Cardiology, University Hospital Groningen (Groningen, The Netherlands), pp. 1208–1213, (Feb 12, 1998).

Pepine, Carl J., MD et al., "Effects of Treatment on Outcome in Midley Symptomatic Patients with Ischemia During Daily Life The Atenolol Silent Ischemia Study (ASIST)," Circulation, American Heart Association Inc. (USA), pp. 762–768, (Jan. 12, 1994).

Hedges, Jerris R., MD, et al., "Prospective Assessment of Presenting Serum Markers for Cardiac Risk Stratification," Acad. Emerg. Med., Hanley & Belfus, Inc. (USA), vol. 3, pp. 27–33, (1996).

Laussac, Jean–Pierre, et al., "Characterization of the Copper(II) –and Nickel(II) –Transport Site of Human Serum Albumin by 13C and 1H NMR Spectroscopy," Biochem, American Chemical Society (USA), vol. 23, pp. 2832–2838, (Jan. 12, 1984).

Predki, Paul F., et al., "Further Characterization of the N–terminal Copper(II) –and Nickel(II) –Binding Motif of Proteins," Biochem J., Department of Biochemistry Research, The Hospital of Sick Children (Toronto, Ontario, Canada), vol. 287, pp. 211–215, (Jan. 12, 1992).

Masuoka, James, et al., "Intrinsic Stoichiometric Equilibrium Constantss for the Binding of Zinc(II) and Copper(II) to the High Affinity Site of Serum Albumin," J. Biol. Chem., The American Society for Biochemistry and Molecular Biology, Inc. (USA), vol. 268, pp. 21533–21537, (Jan. 12, 1993).

Sadler, P.J., et al., "Involvement of a Lysine Residue in the N–terminal Ni2+ and Cu2+ Binding Site of Serum Albumins. Comparison with Co2+, Cd2+ and Al3+," Eur. Biochem., found at http://search19.proxy.aol.com:8000/post–query/MedLine/hrs1994/23450?albumin+n+terminal (USA), PP. 193–200, (Jan. 12, 1994).

Chan, Bernard, et al., "Site–specific N–terminal Auto–degradation of Human Serum Albumin," Eur. J. Biochem., Delta Biotechnology Limited (Nottingham, England), vol. 227, pp. 524–528, (Jan. 12, 1995).

McCord, J. P.H.D., "Oxygen–derived Free Radicals in Post Ischemic Tissue Injury," NEJM, Department of Biochemistry, College of Medicine, University of South Alabama (Mobile, Alabama), vol. 312, pp. 159–163, (Jan. 12, 1985).

Bautista and Mateos–Nevado (1998) Immunological Detection and Quantification of Oxidized Proteins by Labelling with Digoxigenin, Biosci. Biotechnol. Biochem. 62:419–423.

Das and Maulik (1994) Antioxidant Effectiveness in Ischemia–Reperfusion Tissue Injury, Methods in Enzymology 233:601–611.

Davies and Delsignore (1987) Protein Damage and Degradation by Oxygen Radicals, J. Biological Chemistry, 262:9908–9913.

Gutteridge and Wilkins (1983) Copper Salt–Dependent Hydroxyl Radical Formation Damage to Proteins Acting as Antioxidants, Biochimica et Biophysica Acta 759:38–41.

Halliwell and Gutteridge (1986) Oxygen Free Radicas and Iron in Relation to Biology and Medicine: Some Problems and Concepts, Archives of Biochemistry and Biophysics 246:501–514.

Halliwell and Gutteridge (1990) The Antioxidants of Human Extracellular Fluids, Archives of Biochemistry and Biophysics 280:1–8.

Quinlan et al. (1992) Vanadium and Copper in Clinical Solutions of Albumin and Their Potential to Damage Protein Structure, J. Pharmaceutical Sciences 81:611–614.

Röth (1997) Oxygen Free Radicals and Their Clinical Implications, Acta Chirurgica Hungarica 35:302–305.

Stohs (1995) The Role of Free Radicals in Toxicity and Disease, J. Basic and Clinical Physiology and Pharmacology 6:205–228.

Ueda et al. (1995) Reactions of Copper(II)–Oligopeptide Complexes with Hydrogen Peroxide: Effects of Biological Reductants, Free Radical Biology & Medicine 18:929–933.

Vogel et al. (19??) Quant. Chem. Anal. pp. 199–203, Longmans, Green & Co.

U.S. patent application Ser. No. 09/165,961, filed Oct. 2, 1998, pending.

Anderson (1995) "Effects of na+k=2cl Cotransport Inhibition on Myocardial NA and CA During Ischemia and Reperfusion," found at *http://www/uth.tmc.edu/apstracts/1995/cell/September/319c.html*, p. 1.

Chan (1995) Eur. J. Biochem. 227:524.

Cotelle et al. (1992) J. Inorg. Biochem. 46:7.

Davies (1986) J. of Free Radicals in Biology & Med. 2:155–161 and 164–169.

Gomez (1996) "Ruling Out Ischemia Saves Time and Money," vol. 6(9) pp. 148, 150, found at http://www.medscape.com/CPG/ClinRE...c0609.25.gomez/c0609.25.gomez.html, pp. 1–2.

Halliwell (1988) Biochemical Pharmacology 37:569.

Hayakawa (1997) J. of Chromatography B. 698:27.

Huang (1995) "Ischemia–and Reperfusion–Sensitive Cardiac Sympathetic Afferents: Influence of Hydrogen Peroxide and Hydroxyl Radicals," found at *http://www.uth.tmc.edu/apstracts/1995/heart/April/120h.html*, p. 1.

Marx (1985) Biochem. J. 236:397–400.

"New Marker for Exercise–Induced Ischemia," American Assoc. for Clin. Chem., found at http://www.aacc.org/cln/profiles/97profiles/05/diagpro9702.html (1997).

Predki et al. (1992) Biochem. J. 287:211.

QLT Phototherapeutics, Inc., "Product Brochure: Photofrin" Manufactured by Lederle Parenterals, Inc. (Apr. 1996).

Sheat (1991) Clin. Chem. Ref. J. 37:1221.

Sogami (1984), Int. J. Peptide Protein Res. 24:96.

Tucker (1994) Involvement of a Lysine Residue in the N–terminal NI2+ and Cu2+ Binding Site of Serum Albumins found at http://search19.proxy.aol.com:8000/post–query/MedLine/hrs1994/23450?albumin+n++ p. 1, Christopher Ingold Laboratories, University of London, England.

Wysocki (1993) Coronary Artery Disease 4:645.

Brennan et al. (1998) Clinica Chimica Acta 176(2):179–184.

Pepine (1994) J. Myocardial Ischemia 6(3):8–9.

Peters (1996) All About Albumin: Biochemistry, Genetics and Medical Applications *Academic Press* p. 244.

\* cited by examiner

SEQUENCE LISTING

```
<160> NUMBER OF SEQ ID NOS: 3

<210> SEQ ID NO 1
<211> LENGTH: 4
<212> TYPE: PRT
<213> ORGANISM: Homo sapiens

<400> SEQUENCE: 1

Asp Ala His Lys
 1

<210> SEQ ID NO 2
<211> LENGTH: 8
<212> TYPE: PRT
<213> ORGANISM: Homo sapiens

<400> SEQUENCE: 2

Asp Ala His Lys Ser Glu Val Ala
 1               5
```

```
<210> SEQ ID NO 3
<211> LENGTH: 4
<212> TYPE: PRT
<213> ORGANISM: Homo sapiens

<400> SEQUENCE: 3

Ser Glu Val Ala
```

TEST FOR RAPID EVALUATION OF ISCHEMIC STATES AND KIT

BACKGROUND OF THE INVENTION

1. Field of the Invention

The present invention relates to a rapid method for the detection of ischemic states and to a kit for use in such a method. More particularly, the invention relates to the measurement of a bound specific transition element to human serum to determine the presence or absence of ischemia.

2. Discussion of the Background

Ischemia is the leading cause of illness and disability in the world. Ischemia is a deficiency of oxygen in a part of the body causing metabolic changes, usually temporary, which can be due to a constriction or an obstruction in the blood vessel supplying that part. The two most common forms of ischemia are cardiovascular and cerebrovascular. Cardiovascular ischemia, in which the body's capacity to provide oxygen to the heart is diminished, is the leading cause of illness and death in the United States. Cerebral ischemia is a precursor to cerebrovascular accident (stroke) which is the third leading cause of death in the United States.

The continuum of ischemic disease includes five conditions: (1) elevated blood levels of cholesterol and other blood lipids; (2) subsequent narrowing of the arteries; (3) reduced blood flow to a body organ (as a result of arterial narrowing); (4) cellular damage to an organ caused by a lack of oxygen; (5) death of organ tissue caused by sustained oxygen deprivation. Stages three through five are collectively referred to as "ischemic disease," while stages one and two are considered its precursors.

Together, cardiovascular and cerebrovascular disease accounted for 954,720 deaths in the U.S. in 1994. Furthermore, more than 20% of the population has some form of cardiovascular disease. In 1998, as many as 1.5 million Americans will have a new or recurrent heart attack, and about 33% of them will die. Additionally, as many as 3 to 4 million Americans suffer from what is referred to as "silent ischemia." This is a condition where no clinical symptoms of ischemic heart disease are present.

There is currently a pressing need for the development and utilization of blood tests able to detect injury to the heart muscle and coronary arteries. Successful treatment of cardiac events depends largely on detecting and reacting to the presence of cardiac ischemia in time to minimize damage. Cardiac enzymes, specifically the creatine kinase isoenzyme (CK-MB), and cardiac markers, specifically the Troponin I and T biochemical markers, are utilized for diagnosing heart muscle injury. However, these enzymes and markers are incapable of detecting the existence of an ischemic state in a patient prior to myocardial infarction and resulting cell necrosis (death of cell). Additionally, these enzymes and markers do not show a measurable increase until several hours after an ischemic event. For instance, CK-MB, the earlier evident of the two, does not shows a measurable increase above normal in a person's blood test until about four to six hours after the beginning of a heart attack and does not reach peak blood level until about 18 hours after such an event. Thus, the primary shortcoming of using cardiac markers for diagnosis of ischemic states is that these markers are only detectable after heart tissue has been irreversibly damaged.

There currently are no tests available which allow diagnosis of the existence of ischemia in patients prior to tissue necrosis. A pressing requirement for emergency medicine physicians who treat chest pain and stroke symptoms is for a diagnostic test that would enable them to definitively "rule out" myocardial infarction, stroke, and other emergent forms of ischemia. A need exists for a method for immediate and rapid distinction between ischemic and non-ischemic events, particularly in patients undergoing acute cardiac-type symptoms. The present invention provides such a means.

A broader array of diagnostic tests are available for diagnosis of ischemia in patients with non-acute symptoms. The EKG exercise stress test is commonly used as an initial screen for cardiac ischemia, but is limited by its accuracy rates of only 25–50%. Coronary angiography, an invasive procedure that detects narrowing in the arteries with 90–95% accuracy, is also utilized. Another commonly used diagnostic test is the thallium exercise stress test, which requires injection of radioactive dye and serial tests conducted four hours apart. The present invention, however, has the advantage over the known methods of diagnosis in that it provides equivalent or better accuracy at far lower costs and decreased risk and inconvenience to the patient. The present invention provides specificity and sensitivity levels of 75–95%, which are far more accurate than the EKG exercise stress test and comparable in accuracy to current diagnostic standards. Furthermore, the present invention presents a significant time advantage and is cheaper than competing methods of diagnosis by a factor of at least 15 to 1.

It is known that immediately following an ischemic event, proteins (enzymes) are released into the blood. Well known proteins released after an ischemic heart event include creatine kinase (CK), serum glutamic oxalacetic transaminase (SGOT) and lactic dehydrogenase (LDH). One well known method of evaluating the occurrence of past ischemic heart events is the detection of these proteins in a patient's blood. U.S. Pat. No. 4,492,753 relates to a similar method of assessing the risk of future ischemic heart events. However, injured heart tissue releases proteins to the bloodstream after both ischemic and non-ischemic events. For instance, patients undergoing non-cardiac surgery may experience perioperative ischemia. Electro-cardiograms of these patients show ST-segment shifts with an ischemic cause which are highly correlated with the incidence of postoperative adverse cardiac events. However, ST-segment shifts also occur in the absence of ischemia; therefore, electrocardiogram testing does not distinguish ischemic from non-ischemic events. The present invention provides a means for distinguishing perioperative ischemia from ischemia caused by, among other things, myocardial infarctions and progressive coronary artery disease.

SUMMARY OF THE INVENTION

The present need for rapid, immediate and continuous detection of ischemic states is met by the present invention. Specifically, the present invention provides for a rapid method of testing for the existence of and quantifying ischemia based upon method of detecting and quantifying the existence of an alteration of the serum protein albumin which occurs following an ischemic event. Preferred methods of the present invention for detecting and quantifying this alteration include evaluating and quantifying the cobalt binding capacity of circulating blood, analysis and measurement of the ability of serum albumin to bind exogenous cobalt, detection and measurement of the presence of copper in a purified albumin sample and use of an immunological assay sepcific to the altered form of serum albumin which occurs following an ischemic event. Also taught by the present invention is the use of the compound Asp-Ala-His-Lys-R (SEQ ID NO.1), wherein R is any chemical group capable of being detected when bound to any compound capable of binding to the N-terminus of naturally occurring human albumin (including no additional chemical group), for detection and quantification of an ischemic event.

Advantages and embodiments of the invention include a method for ruling-out the existence of an ischemic state or event in a patient; a method for detecting the existence of asymptomatic ischemia; a method for evaluating patients with angina to rule-out the recent occurrence of an ischemic event; an immediate method for evaluation of patients suffering from chest pain to determine the recent occurrence or non-occurrence of a myocardial infarction.; a method for evaluation of patients suffering from stroke-like signs and symptoms to determine the occurrence or non-occurrence of a stroke and to distinguish between the occurrence of an ischemic stroke and a hemorrhagic stroke; a rapid method for supplementing electrocardiographic results in determining the occurrence of true ischemic events; a method for detecting the occurrence of a true ischemic event in a patient undergoing surgery; a method for evaluating the progression of patients with known ischemic conditions; a method for comparing levels of ischemia in patients at rest and during exercise; a method for assessing the efficacy of an angioplasty procedure; a method for assessing the efficacy of thrombolytic drug therapy; a method for assessing the patency of an in-situ coronary stent; and, a method for detecting in a pregnant woman the occurrence of placental insufficiency.

Additional advantages, applications, embodiments and variants of the invention are included in theDetailed Description of the Invention and Examples sections.

As used herein, the term "ischemic event," and "ischemic state" mean that the patient has experienced a local and/or temporary ischemia due to partial or total obstruction of the blood circulation to an organ. Additionally, the following abbreviations are utilized herein to refer to the following amino acids:

| Amino acid | Three-letter abbreviation | Single-letter notation |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A separate test method for ischemia was described by a common inventor in U.S. Pat. Nos. 5,227,307 and 5,290,519 to Bar-Or et al., herein incorporated by reference in their entirety.

BRIEF DESCRIPTION OF THE FIGURES

FIG. 7 illustrates that patients that experience dysrhythmias during PTCA have higher ischemia test values.

DETAILED DESCRIPTION OF THE INVENTION

Figure 1:
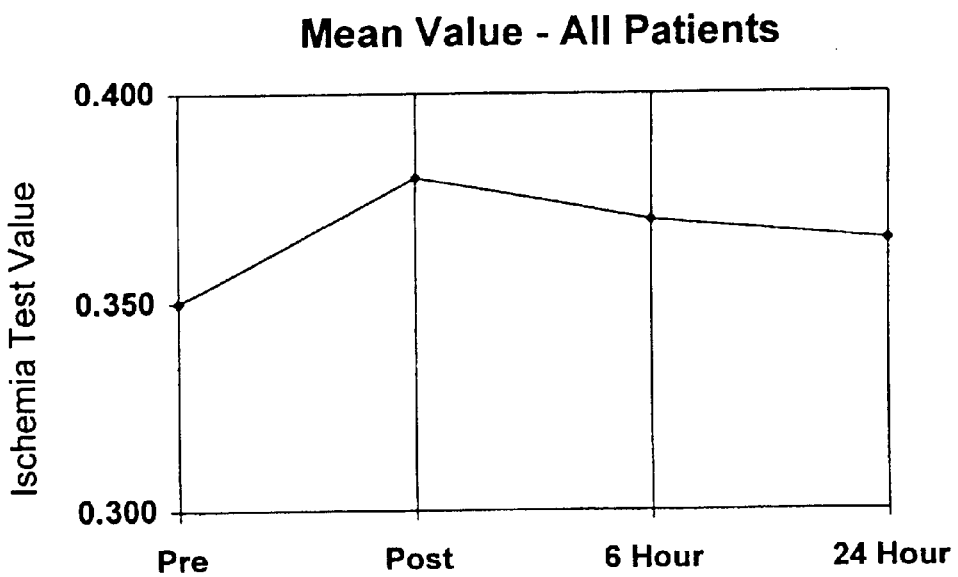
FIG. 1 is a chart illustrating the percentage change in absorbance value in patient samples containing Co ion. The patient samples were taken before percutaneous transluminal coronary angioplasty (PTCA), immediately afger PTCA balloon deflation, 6 hours after the procedure and 24 hours after the procedure, as described in Example 10.
Figure 2:
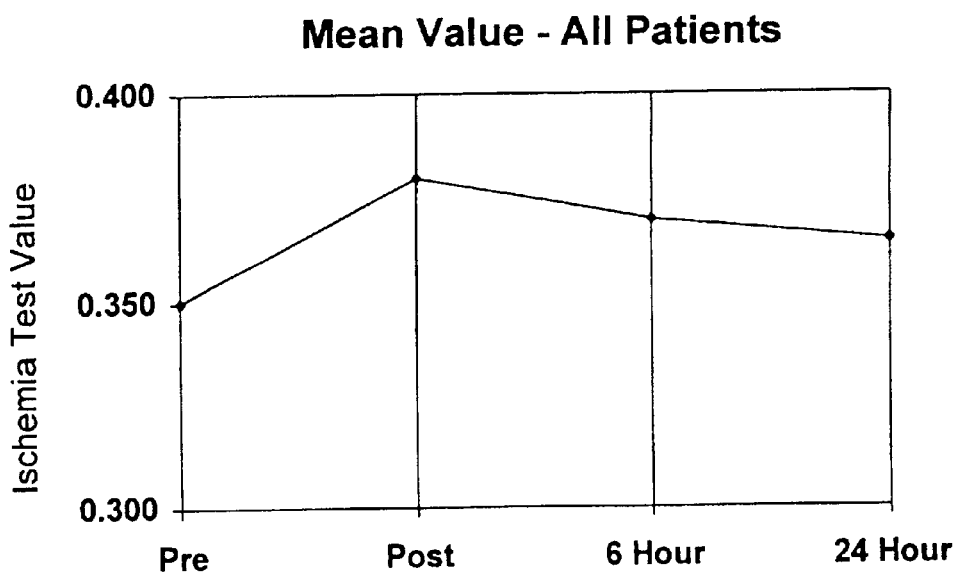
FIG. 2 is a chart setting forth the mean absorbance value in patient samples containing Co ion. The samples were taken before PTCA, immediately after ballon deflation, and 6 and 24 hours after the procedure, as described in Example 10.
Figure 3:
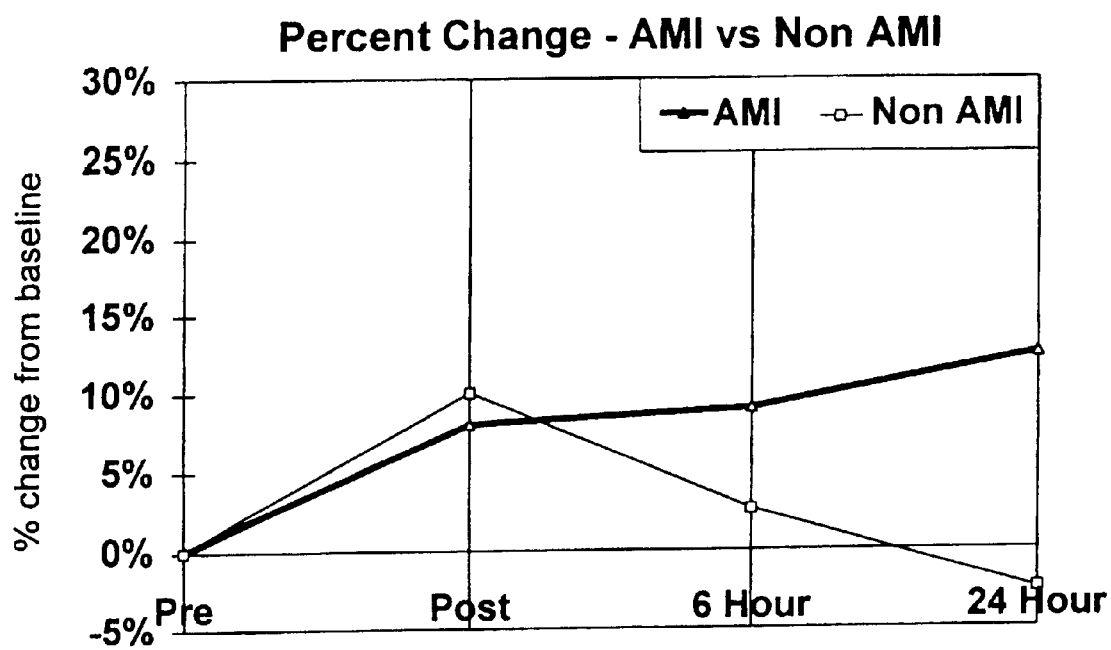
FIG. 3 is a chart illustrating the percentage change in absorbance from baseline of patient samples taken before, immediately after and 6 and 24 hours after PTCA for acute myocardial infarction (AMI) and non-AMI patients. This Figure illustrates that AMI patients have elevated ischemia values that do not return to baseline as quickly as those for non-AMI patients following PTCA, as described in Example 10.
Figure 4:
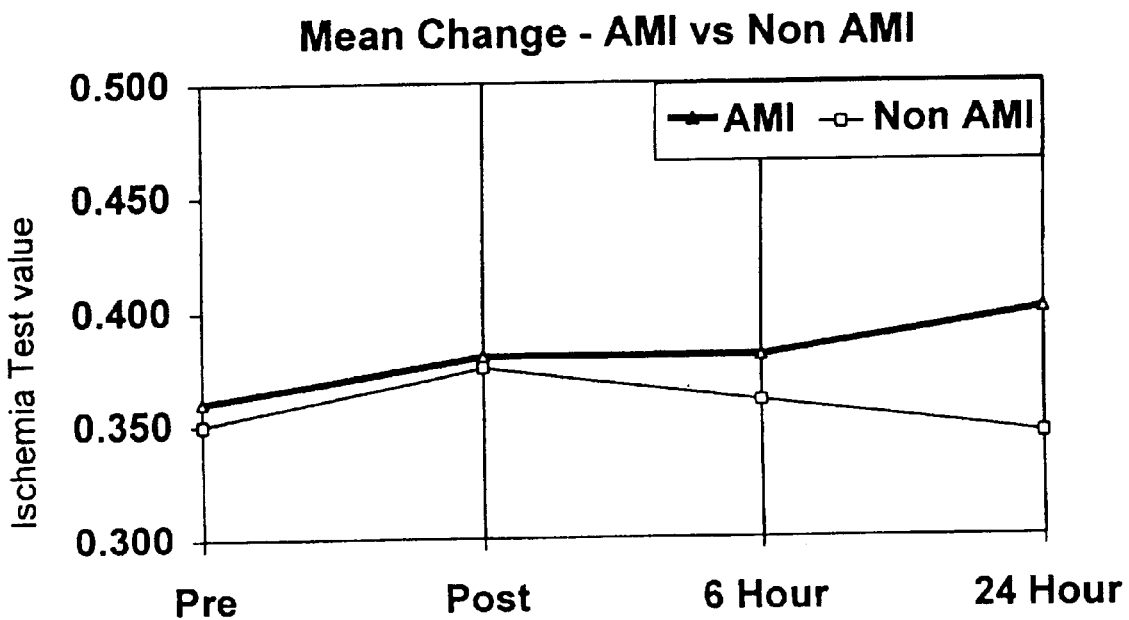
FIG. 4 is a chart illustrating the mean change in absorbance from baseline of patient samples taken before, immediately after and 6 and 24 hours after PTCA for AMI and non-AMI patients, as described in Example 10.
Figure 5:
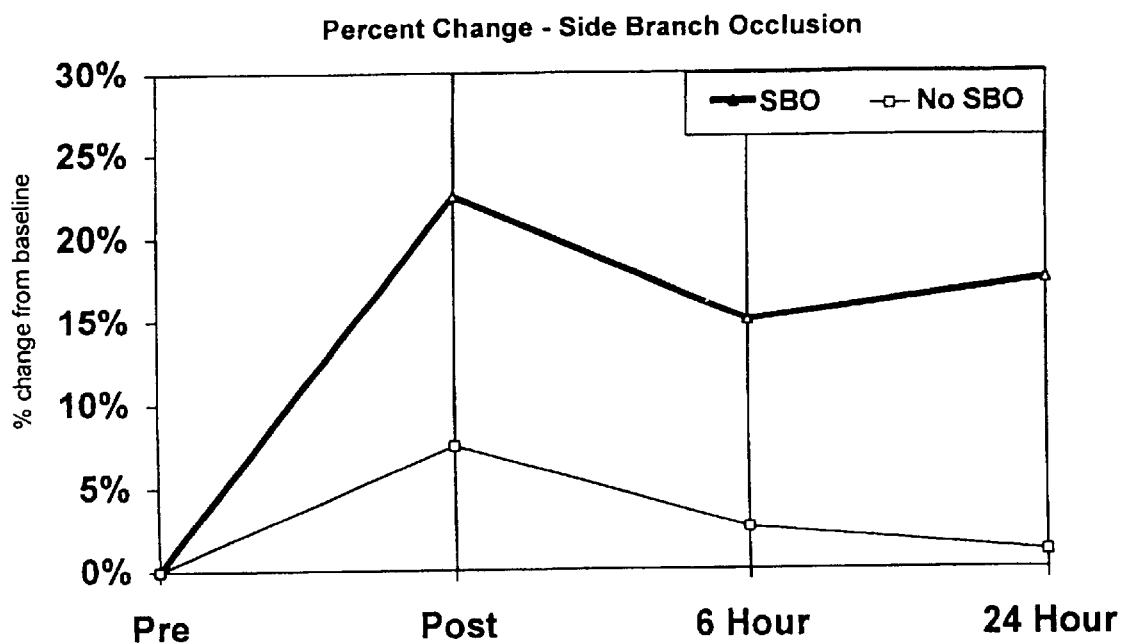
FIG. 5 is a chart illustrating the percentage in absorbance of patient samples taken before, immediately after, and 6 and 24 hours after PTCA change in side branch occlusion (SBO) and non-SBO patients, as described in Example 10. This Figure shows that patients with SBO had higher ischemia test values immediately after and 6 hours after PTCA as compared to non-SBO patients.
Figure 6:
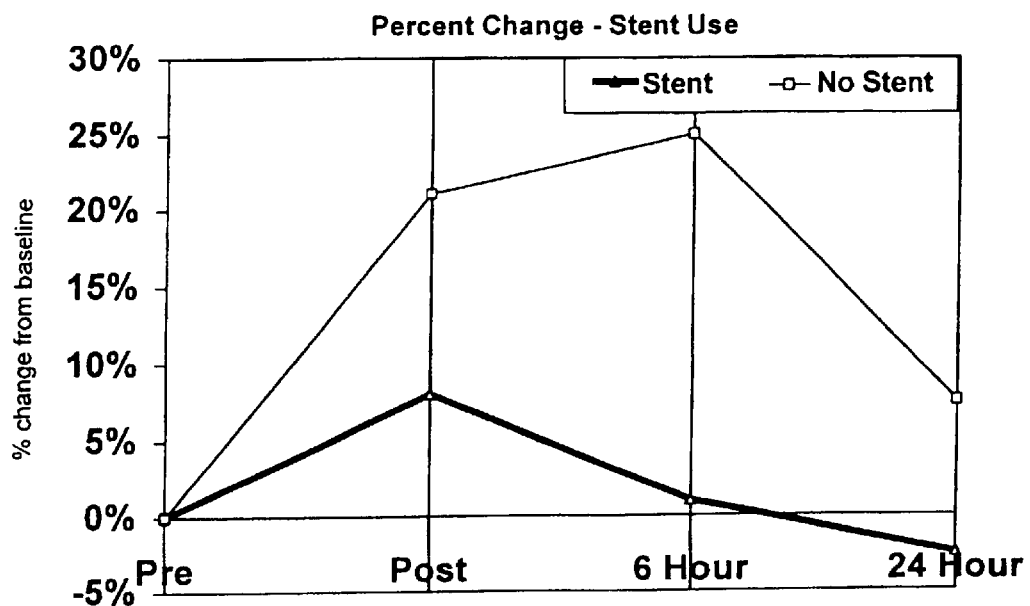
FIG. 6 is a chart illustrating the percentage change from baseline in absorbance of patient samples taken before coronary stent insertion (with PTCA), immediately after, and 6 and 24 hours after stent insertion, and in patients in which no stent was inserted at the time of PTCA, as described in Example 11.

While not being bound by any particular theory, it is believed that the present method works by taking advantage of alterations which occur to the albumin molecule, affecting the N-terminus of albumin during an ischemic ("oxygen-depleted") event. (Ischemia occurs when human tissues are deprived of oxygen due to insufficient blood flow.) A combination of two separate phenomena are believed to explain the mechanism by which the ischemia test of the present invention works. First, it is believed that the localized acidosis which occurs during an ischemic event generates free radicals which alter albumin's N-terminus; thus, by detecting and quantifying the existence of altered albumin, ischemia can be detected and quantified. Second, the acidotic environment present during ischemia results in the release of bound copper (from ceruloplasmin and other copper-containing proteins) which is immediately takenup by albumin. The bound copper also alters the N-terminus of albumin. (Not only does the presence of the complexed copper effectively "alter" the N-terminus, the metal ion damages the protein structure on binding.) Thus, by detecting and quantifying the existence of altered albumin and/or the copper-albumin complexes, ischemia can be detected and quantified.

The details of the first mechanism are believed to be as follows. In the event of an oxygen insufficiency, cells convert to anaerobic metabolism, which depletes ATP, resulting in localized acidosis and lowered pH, and causing a breakdown in the energy cycle (ATP cycle). Cellular pumps that keep calcium against the gradient are fueled by energy from the ATP cycle. With ATP depletion, the pumps cease to function and cause an influx of calcium into the cell. The excess intracellular calcium activates calcium-dependent proteases (calpain, calmodulin), which in turn cleave segments of xanthine dehydrogenase, transforming the segments into xanthine oxidase. The enzymes involved in this process are membrane-bound and exposed to the outside of the cell, and are thus in contact with circulating blood. Xanthine oxidase generates superoxide free radicals in the presence of hypoxanthine and oxygen. Superoxide dismutase dismutates the oxygen free radicals, turning them into hydrogen peroxide. In the presence of metals such as copper and iron which are found in blood, hydrogen peroxide causes hydroxyl free radicals to be formed. Hydroxyl free radicals in turn cause damage to cells and human tissue. One of the substances damaged by free radicals is the protein albumin, a circulating protein in human blood; specifically believed to be damaged is an amino acid chain within the N-terminus of albumin.

Human serum albumin is the most abundant protein in blood (40 g/l) and the major protein produced by the liver. Many other body fluids also contain albumin. The main biological function of albumin is believed to be regulation of the colloidal osmotic pressure of blood. The amino acid and structure of human albumin have been determined. Specifically, human albumin is a single polypeptide chain consisting of 585 amino acids folded into three homologous domains with one free sulfhydryl group on residue #34. The specific amino acid content of human albumin is:

conditions, such as happens during ischemia, ceruloplasmin releases some of its bound copper. The released copper is takenup by albumin. Copper and cobalt both bind to albumin at the same site within the N-terminus. Thus, the bound copper, present during ischemia, blocks cobalt from binding to albumin. The decrease in cobalt binding capacity of circulating blood can be measured and quantified as a means for detecting and quantifying the presence of an ischemic event.

A first method of the present invention comprises a method for detecting the occurrence or non-occurrence of an ischemic event in a patient comprising the steps of: (a) contacting a biological sample containing albumin of said patient with an excess quantity of a metal ion salt, said metal ion being capable of binding to the N-terminus of naturally occurring human albumin, to form a mixture containing bound metal ions and unbound metal ions, (b) determining the amount of bound metal ions, and (c) correlating the amount of bound metal ions to a known value to determine the occurrence or non-occurrence of an ischemic event. In this method, said excess quantity of metal ion salt may comprise a predetermined quantity and the quantity of unbound metal ions is detected to determine the amount of bound metal ions. Additionally, the compound selected from the group consisting of Asp-Ala-His-Lys-R (SEQ ID NO.1), wherein R is any chemical group capable of being detected when bound to any compound capable of binding to the N-terminus of naturally occurring human albumin, may be utilized to facilitate detection.

Preferred embodiments of the first method include samples of serum or plasma, or purified albumin. Preferred embodiments also include use of a metal ion salt comprising a salt of a transition metal ion of Groups 1b–7b or 8 of the Periodic Table of the elements, a metal selected from the group consisting of V, As, Co, Sb, Cr, Mo, Mn, Ba, Zn, Ni, Hg, Cd, Fe, Pb, Au and Ag, or cobalt. Also preferred, is detection of the amount of bound metal ions (or, in the case where the excess quantity of metal ion salt is a predetermined quantity, detection of the quantity of unbound metal

| Bases: | Asp | Asn | Thr | Ser | Glu | Gln | Pro | Gly | Ala | Cys | Val | Met | Ile | Leu | Tyr | Phe | His | Lys | Trp | Arg |
|---|---|---|---|---|---|---|---|---|---|---|---|---|---|---|---|---|---|---|---|---|
| Residues | 39 | 15 | 30 | 22 | 60 | 23 | 25 | 12 | 63 | 35 | 39 | 6 | 8 | 61 | 18 | 30 | 16 | 58 | 1 | 23 |

In one embodiment of the present invention, an excess of cobalt ions are introduced into a purified albumin sample obtained from a patient serum, plasma, fluid or tissue sample. In normal (non-ischemic) patients, cobalt will bind to the amino acid chain on the N-terminus of albumin. In ischemic patients, however, most likely due to the alteration of the binding site of the N-terminus, cobalt binding to albumin is reduced. Accordingly, the occurrence or non-occurrence of an ischemic state can be detected by the presence and quantity of bound or unbound cobalt. Measurement of cobalt can be conducted by atomic absorption, infrared spectroscopy, high-performance liquid chromatography ("HPLC") or other standard or non-standard methods, including radioactive immunoassay techniques.

The details of the second mechanism are believed to be as follows. Ceruloplasmin is a circulating protein which binds copper; approximately ninety-percent of the *in vivo* copper (copper is abundant in blood, with concentrations comparable to iron) will be bound to ceruloplasmin. The remainder is in other bound forms; almost no free copper exists in circulating blood. In acidic conditions and reduced oxygen ions) by atomic absorption or atomic emission spectroscopy or immunological assay. These detection mechanisms are also preferred for determination of the quantity of the compound Asp-Ala-His-Lys-R (SEQ ID NO.1) which is complexed with the metal ion salt in order to detect the quantity of unbound metal ions. A preferred method for conducting said immunological assay is using an antibody specific to an antigen comprising the compound Asp-Ala-His-Lys-R (SEQ ID NO.1), wherein R is said metal ion.

A second method of the present invention is a method of detecting the occurrence or non-occurrence of an ischemic event in a patient comprising the steps of: (a) contacting a biological sample containing albumin of said patient with a predetermined excess quantity of a salt of a metal selected from the group consisting of V, As, Co, Sb, Cr, Mo, Mn, Ba, Zn, Ni, Hg, Cd, Fe, Pb, Au and Ag, to form a mixture containing bound metal ions and unbound metal ions, (b) contacting said mixture with an aqueous color forming compound solution to form a colored solution, wherein said compound is capable of forming color when bound to said metal ion, (c) determining the color intensity of said colored solution to detect the presence of unbound metal ions to provide a measure of bound metal ions, and (d) correlating the amount of bound metal ions to a known value to determine the occurrence or non-occurrence of an ischemic event. Preferred embodiments of this method include the additional step of diluting said colored solution with an aqueous solution isosmotic with blood serum or plasma prior to step (c). Also preferred are: using ferrozine as the color forming compound, and, alternatively, using the compound Asp-Ala-His-Lys-R (SEQ ID NO.1), wherein R is any group capable of forming color when bound to said metal ion as the aqueous color forming compound. Conducting steps (b) and (c) in a pH range of 7 to 9 is preferred. Further, conducting steps (b) and (c) using a spectrophotometer is preferred. Preferred samples in this method also comprise serum, plasma, or purified albumin and a preferred metal ion salt is cobalt.

A third method of the present invention is a method for detecting the occurrence or non-occurrence of an ischemic state in a patient comprising the steps of: (a) detecting the amount of copper ions present in a purified albumin sample of said patient, and (b) correlating the quantity of copper ions present with a known value to determine the occurrence or non-occurrence of an ischemic event. Preferred methods for detection of the amount of copper ions present in the purified albumin sample are by atomic absorption, atomic emission spectroscopy and immunological assay. A preferred method of conducting said immunological assay uses an antibody specific to an antigen comprising the compound Asp-Ala-His-Lys-R (SEQ ID NO.1), wherein R is copper.

A fourth method of the present invention is a method of detecting the occurrence or non-occurrence of an ischemic event in a patient comprising the steps of: (a) contacting a purified albumin sample of said patient, with an aqueous color forming compound solution to form a colored solution, wherein said compound is capable of forming color when bound to copper, (b) determining the color intensity of said colored solution to determine the amount copper in said sample, and (c) correlating the amount of copper to a known value to determine the occurrence or non-occurrence of an ischemic event. Preferred embodiments of this method include the additional step of diluting said colored solution with an aqueous solution isosmotic with blood serum or plasma prior to step (b). Also preferred are: using ferrozine as the color forming compound, and, alternatively, using the compound Asp-Ala-His-Lys-R (SEQ ID NO.1), wherein R is any group capable of forming color when bound to copper ion as the aqueous color forming compound. Conducting steps (a) and (b) in a pH range of 7 to 9 is preferred. Further, conducting step (b) using a spectrophotometer is preferred.

Applications, embodiments and methods of the present invention comprising one or more of the aforementioned four methods of the present invention include: a method for ruling-out the existence of ischemia in a patient, comprising application of either of the aforementioned methods, including application of any of the methods wherein said patient possesses one or more cardiac risk factors, said cardiac risk factors being selected from the group consisting of: age greater than 50, history of smoking, diabetes mellitus, obesity, high blood pressure, high cholesterol, and strong family history of cardiac disease. A variant thereof, comprises subjecting the patient to an exercise treadmill test followed by a second application of the method of claim 1, followed by a comparison of the results of the two applications. This method may be used to detect the existence of ischemia provoked by exercise in an otherwise asymptomatic patient.

Other embodiments, applications and variants of the present invention include a method for ruling-out the occurrence of an temporally-limited ischemic event in a patient comprising application of the method of claim 1; a method of detecting the existence of ischemia in an asymptomatic patient comprising application of the method of claim 1; a method for the evaluation of patients suffering from stroke-like signs to determine the occurrence or non-occurrence of a stroke, comprising application of the method of claim 1; a method for distinguishing between the occurrence of an ischemic stroke and a hemorrhagic stroke, comprising application of the method of claim 1; and a method for assessing the efficacy of an angioplasty procedure, comprising application of the method of claim 1.

The present invention also provides a method for evaluation of a patient presenting with angina or angina-like symptoms to detect the occurrence or non-occurrence of a myocardial infarction, comprising application of the method of claim 1 and application of an electrocardiographic test, followed by correlation of the results of the application of the method of claim 1 with the results of the electrocardiographic test to determine the occurrence or non-occurrence of a myocardial infarction. Preferred electrocardiographic tests are E.C.G., E.K.G. and S.A.E.C.G. tests.

Another method of the present invention is a method for supplementing electrocardiographic results to determine the occurrence or non-occurrence of an ischemic event, comprising application of the method of claim 1 and application of an electrocardiographic test, followed by correlation of the results of application of the method of claim 1 with the results of said electrocardiographic test to determine the occurrence or non-occurrence of an ischemic event. A variant thereof, comprises application of the method wherein said patient is undergoing surgery.

A further method of the present invention is a method for comparing levels of ischemia in patients at rest and during exercise is also taught by the present invention, comprising application of the following steps at designated time intervals: (a) application of the method of claim 1, (b) administration of an exercise treadmill test followed by a second application of the method of claim 1, and (c) comparing the results of the application of the method of claim 1 prior to administration of the exercise treadmill test with the results of the application of the method of claim 1 after administration of the exercise treadmill test, wherein, results obtained from said steps are correlated with results obtained at prior designated time intervals. This embodiment may be used to evaluate patients with known or suspected ischemic conditions, to assess the patency of an in-situ coronary stent and to assess the efficacy of an angioplasty procedure. Preferred designated time intervals are three months, six months or one year.

The present invention also teaches a method for assessing the efficacy of thrombolytic drug therapy, comprising the method of claim 1; a method for detecting in a pregnant woman the occurrence of placental insufficiency, comprising application of the method of claim 1.

A greater understanding of the present invention and of its many advantages may be had from the following examples, given by way of illustration. The following examples are illustrative of some of the methods, applications, embodiments and variants of the present invention. They are, of course, not to be considered in any way limitative of the invention. Numerous changes and modification can be made with respect to the invention.

EXAMPLE 1

Sample Handling Procedures for Ischemia Testing

The sample which may be used in the present invention may be obtained from any tissue or fluid sample taken from a patient, or from commercial vendor sources. Appropriate fluid samples include whole blood, venous blood, arterial blood, blood serum, plasma, as well as other body fluids such as amniotic fluid, lymph, cerebrospinal fluid, saliva, etc. The sample may be obtained by well known conventional biopsy and fluid sampling techniques. Preferred samples are blood plasma and serum and purified albumin. Purified albumin may be isolated from the serum by any of the known techniques, which would include electrophoresis, ion exchange, affinity chromatography, gel filtration, etc.

Blood samples are taken using Universal Precautions. Peripheral venipuncture is performed with the tourniquet on less than 30 seconds (contralateral arm from any IV fluids). Blood is drawn directly into two 10 cc Becton Dickinson Vacutainer® Sodium-Heparinized tubes. Gently invert once to mix. If an IV port is used, the blood can be collected (after a discard sample is drawn equivalent to the dead space of usually 5 cc) into a plain syringe and dripped gently down the side of two 10 cc Becton Dickinson Vacutainer® brand tubes. Gently invert once to mix. Blood may also be collected directly from the Vacutainer® tubes with special administration sets with a reservoir system that do not require a discard sample. These systems allow a draw to be taken proximal to the reservoir.

Plasma tubes must be centrifuged within 2 hours of the draw. (Note, if serum is collected, it must clot between 30–120 minutes at room temperature (RT) before centrifugation. Ring the inside of the serum tube with a wooden applicator to release the clot from the glass before centrifugation. If the subject is taking anti-coagulants or has a blood clotting dysfunction, clot longer than 60 minutes, between 90–120 minutes best.) Centrifuge tubes for 10 minutes at RT at 1100 g (<1300 g). Pool collected samples in a plastic conical tube and invert once to mix.

If the sample will not be used within 4 hours of centrifugation, the sample should be frozen. Alternatively, separated serum may be refrigerated at 4° C. until tested, but should be tested within 8 hours (storage over 24 hours may result in degradation of the sample). "Stat" results (obtained within 1 hour of completion of centrifugation step) are preferred. The following percent differences for the ischemia test were measured using plasma and serum samples $\leq 8$ hours and $\leq 24$ hours after collection. Delayed test results were compared to stat test results on the same patient sample and the mean percent differences (and standard deviations) were as given below:

Storage and Delayed Testing Data for the Ischemia Test

|  |  | $\leq$8 hrs. vs. stat |  | $\leq$24 hr. vs. stat* |
|---|---|---|---|---|
| Plasma | n | 20 | n | 23 |
| (stored at | % diff | −5.3% | % diff | −4.8% |
| room temp) | S.D. | .094 | S.D. | .090 |
| Plasma | n | 18 | n | 40 |
| (stored at | % diff | 1.7% | % diff | 1.0% |
| 4° C.) | S.D. | .070 | S.D. | .094 |
| Serum | n | 16 |  |  |
| (stored at | % diff | −12.8% | (not enough |  |
| room temp) | S.D. | .157 | samples) |  |
| Serum | n | 14 | n | 24 |
| (stored at | % diff | −7.3% | % diff | −2.7% |
| 4° C.) | S.D. | .040 | S.D. | .210 |

*$\leq$24 hr. test results given here are a total that include the $\leq$8 hr. test sample results.

EXAMPLE 2

Test Method for Detecting Occurrence of Ischemic Event Using Cobalt Binding

The ischemia test (cobalt version) may be run as follows: 200 $\mu$l of patient sera is added to each of two tubes each containing 50 $\mu$l 0.1% $CoCl_2 \cdot 6H_2O$. The mixture is allowed to react at room temperature (18–25° C.), or higher, for 5 or more minutes. Thereafter 50 $\mu$l 0.01 M dithiothreitol (DTT) is added to one of the two tubes (the "test tube") and 50 $\mu$l 0.9% NaCl is added to the second tube (the "background tube"). After two minutes, 1 ml 0.9% NaCl is added to both tubes. A470 spectroscopy measurements are taken of the two tubes. The ischemia test was considered positive if the optical density was greater than or equal to 0.400 OD (or alternatively a clinically derived cut-off) using a spectrophotometer at OD 470 nm.

Equivalent materials which may be used as alternatives include any of the transition metals. Ferrozine or other compounds with an affinity to cobalt can be substituted for DTT and/or any cobalt or metal coloring reagent. $CoCl_2 \cdot 6H_2O$, for instance, can be utilized. The optimal range for cobalt binding to albumin is from pH 7 to pH 9, with a range of pH 7.4–8.9 being most preferred; pH 9 is optimal for cobalt interaction with the color reagent. The amount of serum sample can also vary, as can the amounts of $CoCl_2 \cdot 6H_2O$ and DTT and ferrozine. Critical, however, is that the amount of cobalt used be in excess of the amount of albumin and that the DTT or ferrozine be in excess of the cobalt.

EXAMPLE 3

Test Method For Detecting Occurrence of Ischemic Event Using Measurement of Copper Albumin was purified from 0.2 cc of human serum or plasma using an ion exchange method to produce approximately 8 mg of purified albumin. A buffer having a pH in the range of 7 to 9 is added. The amount of copper present in the sample is then measured by direct spectrophotometric and potentiometric methods, or by any of several other known methods, including atomic absorption, infrared spectroscopy, HPLC and other standard or non-standard methods, including radioactive tracer techniques. The proportion of copper to albumin can be then used as a measure of ischemia, the greater the proportion, the higher the ischemia value.

EXAMPLE 4

Test Method for Ruling-out The Existence of Ischemia in a Patient

The following protocol is designed to rule out ischemic conditions in healthy appearing patients who describe prior symptoms of occasional chest pain or shortness of breath.

First, a medical history (including a detailed history of the present and past medical problems and risk factors for ischemic heart disease), physical exam, and vital signs are obtained. If the patient has any cardiac risk factor for ischemic heart disease (age>50, smoking, diabetes mellitus, obesity, high blood pressure, elevated low density lipoproteins, high cholesterol, and strong family history of cardiac disease), the physician is instructed to order a resting twelve-lead EKG and a chest x-ray. If the twelve-lead EKG shows evidence of an acute myocardial infarction (AMI), the patient is immediately transported to a hospital for intensive cardiac treatment. If the twelve-lead EKG does not show evidence of (AMI), the patient will be scheduled for an outpatient twelve-lead EKG exercise treadmill within the next few days. A blood sample should be drawn immediately before and again after the exercise treadmill test and the ischemia test run on each sample.

If the exercise treadmill test shows definite evidence of cardiac ischemia, usually seen by characteristic changes of the ST segments, dramatic abnormalities of pulse or blood pressure, or anginal chest pain is present, the patient should be treated for cardiac ischemia and referred to a cardiologist for possible coronary angiogram and angioplasty. If the exercise treadmill test does not show any evidence of cardiac ischemia, or the findings are equivocal, but the ischemia test is abnormal, the patient similarly should be treated for cardiac ischemia and referred to a cardiologist for possible coronary angiogram and angioplasty. (Absent the present invention, such patients with moderate to high cardiac risk factors would be referred to a cardiologist for further (typically invasive) cardiac testing.

If the exercise treadmill test does not show any evidence of ischemic heart disease, or the findings are equivocal, and the ischemia test is normal, the patient may be sent home with no evidence of cardiac ischemia. In comparison, prior to the present invention, in the case where the exercise treadmill test does not show any evidence of cardiac ischemia, or the findings are equivocal, patients with low risk for cardiac ischemia typically would not have any other tests ordered. In such cases, the physician is taking a calculated risk. It is well documented in the medical literature that at least 25 to 55 percent of patients (higher in females) will have some ischemic heart disease which is not found with routine exercise treadmill testing.

EXAMPLE 5

Test Method for Evaluating Patients with Angina to Rule-out the Occurrence of an Ischemic Event In this study, clinical criteria (EKG changes, elevated cardiac enzymes or markers, positive thallium treadmill or positive angiogram) were used to determine the presence or absence of ischemia in patients presenting with chest pain. Ischemic patients were those with at least one clinical finding positive for ischemia. Normal patients were those for whom clinical findings were negative, as well as normal volunteers with no history or symptoms of cardiac or cerebral ischemia.

Blood samples were taken from 139 subjects who either presented to emergency departments of several hospitals with chest pain or normal volunteers. Blood was drawn into plain red top tubes and, after ten minutes, the clotted blood was centrifuged to separate the serum. Serum was refrigerated at 4° C. until tested. If the sample would not be used within 4 hours of centrifugation, it was frozen, but in no case was testing delayed more than 3 days.

Samples were centrifuged for 5–10 minutes in an analytical centrifuge immediately before testing. 200 µl off each sample was aliquoted in triplicate with an additional tube to be used as a Blank (no DTT) control into borosilicate glass tubes. Also aliquoted was 200 µl of a Standard, such as Accutrol or HSA, in triplicate plus a Blank control. At 10 second intervals, 50.0 µl of 0.10% $CoCl_2$ (store working stock and stock at 4° C.) was added to each tube. Solution was added to the sample, not glass, and tubes were "flicked" to mix.

After 10.0 minutes (starting with the first tube to which cobalt solution was added) an additional 50.0 µl of 0.9% NaCl was added to the two Blank tubes using the appropriate 10 second intervals. 50.0 µl of 0.01 M DTT was additionally added to the Plasma (not Blank) tubes in their appropriate 10 second intervals. Of note, it is prefered that DTT be made fresh weekly (6 mg per 4 ml $H_2O$) and stored at 4° C.

After 2 minutes (starting with the first tube to which cobalt solution was added) 1.0 ml. of 0.9% NaCl solution was added to each tube, using the appropriate 10 second intervals. Tubes were agitated to mix. In the event that that there were too many tubes to finish the test tubes in 10 second intervals, reagents were added to the "Blank" tubes without timing.

The optical density of each sample set was read using the set's Blank to read absorbance at 470 nm. The cuvette was checked for air bubbles before reading and washed with $H_2O$ between sets. The ischemia test was considered positive if the optical density was greater than or equal to 0.400 using the spectrophotometer at OD 470 nm.

The results of the ischemia test compared to the diagnosis determined by clinical criteria are as described in the chart below. Four false negatives and three false positives were reported.

| Clinical Diagnosis | Ischemia Test | |
| --- | --- | --- |
| | + | − |
| + | 99 | 95 | 4 |
| − | 40 | 3 | 37 |

Study results demonstrated that the ischemia test marker has a higher value in patients with clinically diagnosed ischemia. The diagnostic accuracy of the ischemia test for the chest pain study was above 90 percent (sensitivity, 96.0%; specificity, 92.5%; predictive value, (+)96.9%; predictive value, (−)90.2%).

EXAMPLE 6

Test Method For Evaluation of Patients Suffering From Chest Pain to Determine the Occurrence or Non-occurrence of a Myocardial Infarction The following study is proposed to test the ability of the present invention to detect ischemia in the initial hours following the onset of chest discomfort suspicious for cardiac ischemia. The cobalt version of the test is used.

The patient population is limited to male or female persons, 30 years or older, who present to the Emergency Department with complaints of chest discomfort of less than four hours in duration for reasons independent of the study. Patients will be excluded from the study if they met any of the following criteria: (1) known concurrent non-cardiac ischemic disease(s), including but not limited to transient ischemic attacks, cerebral vascular accident, peripheral vascular disease, intermittent claudication, bowel ischemia, and severe renal failure; (2) definite radiological evidence of a cause of chest discomfort that is other than cardiac ischemia, such as, but not limited to, pneumonia, pneumothorax, and pulmonary embolus; or (3) chest discomfort temporally related to local trauma.

All standard evaluation and treatment appropriate for emergency department patients with suspected cardiac ischemia will be followed at all times. The drawing of blood for the study will not in any manner modify the standard treatment protocol. Within these parameters, a pre-treatment evaluation was conducted, which included documentation of all current medications, documentation of previous medical history, EKG, laboratory and radiographic test results, and documentation of most recent vital signs and a physical examination.

The study consists of drawing an extra blood sample at the time of admission to the emergency department. Samples are collected from a catheter that was already in place for intravenous access or alternatively by venipuncture. Collection and administration of the ischemia test is as described in Example 6 herein.

EXAMPLE 7

Test Method For Detection of Ischemia in Patient at Rest and During Exercise

The primary objective of this trial is employ and test the sensitivity of the ischemia test at various time points, before, during and after an exercise thallium treadmill test. Preliminary data has shown that the blood level of the ischemia test rises immediately after an ischemic event. The purpose of this pilot investigation is to determine the magnitude of this rise in level of the ischemia test during a test to define the presence or absence of a cardiac ischemic event, said test being the exercise thallium treadmill test. While it is possible that patients scheduled for exercise thallium treadmill test may have already experienced an ischemic event, preliminary data indicates that a further, significant decline in cobalt binding (and an increase in the ischemia test serum level) will occur if tissue ischemia is induced during the exercise thallium treadmill test.

Patients already scheduled for an exercise thallium treadmill test were asked to give their consent for participation which required two tubes of blood (20 cc's) to be drawn up to 5 (five) times before, during and after the exercise thallium treadmill test. Eligible patients consisted of patients who met all of the following criteria: (1) Age: 18 years or older; (2) Male or female; (3) able to provide written informed consent; and (4) referred for exercise thallium treadmill test for reasons independent of this investigation. Patients were excluded from participation in the study if they met any of the following criteria: (1) known concurrent non-cardiac ischemic disease including, but not limited to: transient ischemic attacks, cerebral vascular accident, acute myocardial infarction and intermittent claudication; (2) inability to complete the standard protocol for the exercise portion of the exercise thallium treadmill test; or (3) cardiac arrest during the exercise portion of the exercise thallium treadmill test.

Prior to administration of the exercise thallium treadmill test, a pretreatment evaluation was conducted which included documentation of all current medications, documentation of previous medical history, EKG, laboratory and radiographic test results, and documentation of most recent vital signs and physical examination.

The standard exercise thallium treadmill test procedure was followed at all times. In no instance was the drawing of the additional blood samples for the purpose of the study permitted to subject the patient to additional risk (beyond the drawing of blood), or to in any manner modify the treatment of the patient.

The "standard" exercise thallium treadmill test procedure comprised generally the following: The patient is brought to the exercise test room in a recently fasting state. After initial vital signs and recent history are recorded, the patient is connected to a twelve-lead EKG monitor, an intravenous line is established and the patient is instructed in the use of a treadmill. With the cardiologist in attendance, the patient walks on the treadmill according to the standard Bruce protocol: starting at a slow pace (approx. 1.7 mph) and gradually increasing both the percent grade (slope) of the treadmill and the walking speed at three minute intervals up to a maximum of 5.5 mph at 20° grade. Termination of the exercise portion on the exercise thallium treadmill test may occur at the discretion of the cardiologist based on patient symptoms, EKG abnormalities, or the attainment of $\geq 85\%$ maximal heart rate.

With the patient near maximal effort on the treadmill, approximately 3 mCi of thallium $^{201}$ is injected intravenously while the patient continues to exercise for approximately one more minute. At the end of exercise, single photon emission computerized tomography (SPECT) is used to scan the patient's myocardium for any perfusion defects. Following recovery, between 2 and 4 hours after exercise, a smaller amount of thallium $^{201}$ (approximately 1.5 mCi) is re-injected for repeat SPECT scan. EKG's and SPECT scans are analyzed for ischemic criteria. The SPECT scans may show fixed and reversible perfusion defects. The reversible perfusion defects indicate ischemia and the fixed defects indicate myocardial scarring.

The study consisted of drawing blood samples on 3 occasions during the exercise thallium treadmill procedure. Two tubes of blood (approximately 4 teaspoons) were collected before the exercise test, immediately after exercise, between 1 and 4 hours after exercise. Blood samples were collected from the catheter already in place for the exercise thallium treadmill procedure or alternatively by venipuncture. Note: Radiation Protection/Safety Considerations—Blood drawn following thallium $^{201}$ injection is routinely considered safe because the amount injected is approximately 3 mCi and, for all practical purposes, the dilution into the systemic circulation reduces the sample level to less than 0.67 nanoCi per cc.

Standard patient follow-up was conducted according to clinical practice. Patients who had subsequent coronary angiograms after being enrolled in this exercise thallium treadmill test study had all resultant coronary angiogram information obtained recorded to verify the exercise thallium treadmill test results.

All clinical and research laboratory testing procedures were performed in a blinded fashion.

Of the 59 patients enrolled (plasma and serum samples tested by the ischemia test method), 11 patients were deleted because of one of the following reasons: a chronically occluded coronary artery and no sample collected later than one hour after exercise, a clinical history of exercise leg pain (claudication), hemolyzed baseline blood samples, patient did not continue with the exercise study or did not agree to further blood tests, patient received an exercycle thallium test instead of a treadmill thallium test and one patient whose chest pain was later determined to be due to pneumonia.

Of the remaining 48 patients, 23 had no history of known ischemic heart disease, 23 had prior ischemic heart disease requiring angioplasty or coronary artery bypass grafts and 2 had prior myocardial infarctions but did not receive angioplasty or coronary artery bypasss grafts. In the subgroup of 23 patients with no prior history of ischemic heart disease (using a total outcome score of $\geq 9$ and a $\geq 4.7\%$ increase in Ischemia Test values either one or three hours after exercise as positive for ischemia) there were 2 true positives, 15 true negatives, 6 false positives and 0 false negatives for a sensitivity of 100% and a specificity of 72%.

Using the same criteria for positive exercise thallium treadmill and Ischemia Test results, the entire 48 patients (including patients with and without a prior history of ischemic heart disease) had 6 true positives, 29 true negatives, 11 false positives and 2 false negatives for a sensitivity of 75% and a specificity of 73%.

Changing the positive criteria to a total thallium treadmill outcome score of $\geq 10$ and a $\geq 5.4\%$ increase in Ischemia Test values one hour after exercise for the entire 48 patients (including patients with and without a prior history of ischemic heart disease) gave 3 true positives, 37 true negatives, 7 false positives and 1 false negative for a sensitivity of 75% and a specificity of 88%.

EXAMPLE 8
Assessing Efficacy of an Angioplasty Procedure

Percutaneous transluminal coronary angioplasty ("PTCA"), also referred to as coronary artery balloon dilation or balloon angioplasty, is an established and effective therapy for some patients with coronary artery disease. PTCA is an invasive procedure in which a coronary artery is totally occluded for several minutes by inflation of a balloon. The inflated balloon creates transient but significant ischemia in the coronary artery distal to the balloon. The result, however, is a widening of a narrowed artery.

PTCA is regarded as a less traumatic and less expensive alternative to bypass surgery for some patients with coronary artery disease. However, in 25 to 30 percent of patients, the dilated segment of the artery renarrows within six months after the procedure. In these cases, either repeat PTCA or coronary artery bypass surgery is required. Additionally, complications from angioplasty occur in a small pertcentage of patients. Approximately, 1 to 3 percent of PTCA patients require emergency coronary bypass surgery following a complicated angioplasty procedure.

The present invention addresses both problems by providing a means for monitoring on-going angioplasty procedures and by providing a mechanism for monitoring the post-angioplasty status of patients.

Twenty-eight patients already scheduled for emergent or elective angioplasty had blood samples (20 ml) drawn just prior to undergoing PTCA ("baseline") at 6, 12 and 24 hours after the last balloon deflation, and three tubes (25 ml) at 1 minute and 6 minutes after the last balloon deflation. Collection and administration of the test was as described in Example 6 herein. A detailed description of the angioplasty procedure was also recorded so the magnitude of 'downstream' ischemia could be estimated. This included catheter size, number of inflations, inflation pressure, duration of inflation, number of vessels involved and location.

The eligible patient population consisted of male or female patients who met all of the following criteria: (1) 18 years or older; (2) referred for PTCA for reasons independent of the study; (3) able to give written, informed consent; and (4) and did not possess any of the exclusionary criteria. Patients were excluded if they met any of the following criteria: (1) patients who were to have PTCA performed with a perfusion catheter; (2) patients with known, concurrent ischemic disease including, but not limited to transient ischemic attacks, cerebral vascular accident, acute myocardial infarction and intermittent claudication. Prior to PTCA, a pretreatment evaluation was conducted which included documentation of all concurrent medications and the taking of a blood sample for ischemia test administration and baseline (this occurred after the patient had been heparinized and the sheath placed).

The standard PTCA protocol was followed at all times. In no instance was the drawing of the additional tubes of blood permitted to subject the patient to additional risk (beyond the drawing of the blood), or modify the standard protocol.

The "standard" PTCA protocol generally comprised the following: The patient was transported to the cardiac catheterization laboratory in the fasting state. The right groin draped and prepped in the usual sterile fashion. Local anesthesia was administered consisting of 2% lidocaine injected subcutaneously and the right femoral artery entered using an 18 gauge needle, and an 8 French arterial sheath inserted over a guide wire using the modified Seldinger technique. Heparin, 3000 units, was administered I.V. Left coronary cineangiography was performed using Judkins left 4 and right 4 catheters, and left ventricular cineangiography performed using the automated injection of 30 cc of radiocontrast material in the RAO projection. After review of the coronary angiography, PTCA was performed.

The diagnostic cardiac catheter was then removed from the femoral sheath and exchanged for a PTCA guiding catheter which was then positioned in the right or left coronary ostia. An additional bolus of intravenous heparin, 10,000 units, was administered. A coronary guidewire, usually a 0.014 inch flexible tipped wire, was then advanced across the obstruction and positioned distally in the coronary artery. Over this guidewire, the balloon inflation system was inserted, usually consisting of a "monorail" type balloon dilation catheter. Sequential balloon inflations were made, with angiographic monitoring between inflations. The duration of the inflations varied among operators, but averaged approximately 45–60 seconds; occasionally prolonged inflations between 3 and 15 minutes were performed.

When it was determined that adequate opening of the coronary stenosis had been achieved, the balloon catheter was fully withdrawn and coronary angiograms performed with and without the guidewire in position. If no further intervention was believed to be necessary, the sheath was then sewn into position and the patient transported to either the intensive care unit or observation unit. The sheath was removed after approximately 6 hours and firm pressure applied with a C clamp or manual pressure. The patient remained at bed rest for approximately 6 hours after sheath removal.

Standard patient follow up was conducted according to clinical practice.

As stated, sample collection and administration of the ischemia test occurred essentially as described in Example 6 herein. The test technician was masked to the time the PTCA sample was taken.

Compared to baseline, 26 of the 28 tested patients demonstrated increased ischemia values after balloon inflation. The remaining two patients registered false negatives, both of which started with baseline values above 0.400. The mean increase in the ischemia test value from baseline to balloon inflation was 15.2%. Of the 21 patients that had 5 hour samples tested, all but three demonstrated a decreased ischemia test value compared to that measured during balloon inflation. Study results demonstrated that the ischemia test marker rises almost immediately following controlled onset of ischemia during the angioplasty procedure. The rapid rise of the marker during balloon inflation and its descent over a five hour period correlated with the controlled start and stop of ischemia. The diagnostic accuracy of the study was 96 percent.

EXAMPLE 9
Evaluation of Post-Myocardial Infarction Patients

In a second study, three subsets of patients—patients without acute myocardial infarction (NonAMI), patients with acute myocardial infarction (AMI), and patients without AMI with significant collateral circulation (NonAMI collateral)—all of whom were undergoing emergent or elective angioplasty had blood samples collected prior to PTCA, immediately after balloon deflation, 6 hours after the procedure, and 24 hours after the procedure. A total of 63 patients were tested. The standard PTCA protocol (as described in Example 9) was followed.

During PTCA, blood was drawn into a syringe and then transferred to sodium-heparinized tubes. Post PTCA samples were drawn into green top sodium-heparinized tubes. In all other regard, sample collection and administration of the ischemia test occurred essentially as described in Example 6 herein. The test technician was masked to the time the PTCA sample was taken.

The ischemia test was considered positive if it increased between baseline and immediately after balloon angioplasty. The results of the study showed a statistically significant a rise (p=0.000 1) in the ischemia test marker following balloon angioplasty and a return to baseline within 24 hours. The mean percent increase for all patients in the study was 9.4%.

excludes patients in the NonAMI collateral subset. The number of patients varies because investigators were not always able to obtain blood samples at all four draw times. A subset of patients who had all data points showed no difference from the total patients.

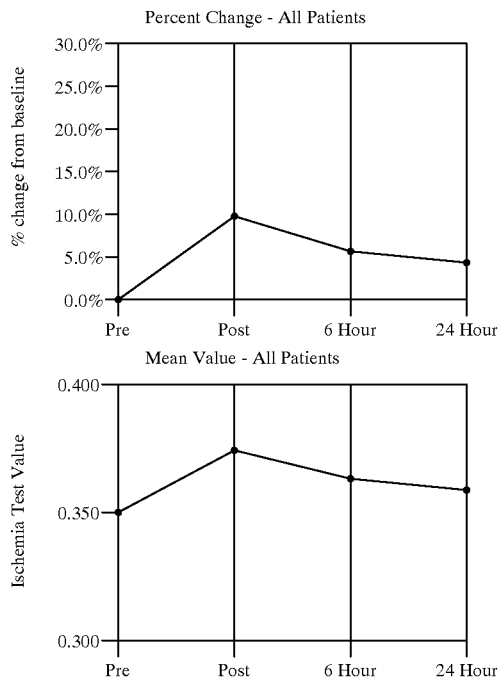

| TIME POINT | N | MEAN | SD | MEAN DIFF FROM BASELINE | SD | MEAN % DIFF FROM BASELINE | SD | P-VALUE |
|---|---|---|---|---|---|---|---|---|
| Baseline | 62 | .354 | .0424 | — | — | — | — | — |
| Immed. post PTCA | 63 | .385 | .0411 | .0310 | .0382 | 9.4% | .1178 | .0001 |
| 6 hours post PTCA | 57 | .368 | .0513 | .0150 | .0505 | 5.0% | .1507 | .0167 |
| 24 hours post PTCA | 43 | .363 | .0474 | .0090 | .0444 | 3.2% | .1312 | .1221 |

Patients with AMI were predicted to have ischemia test values that would not return to baseline as quickly as those in the NonAMI subset. Patients were assigned to the AMI subset if there was evidence in the medical record of a new AMI in the 72 hours prior to PTCA. Assignment was made by the study's principal investigator, a practicing cardiologist who was masked to all study results.

The results showed significantly higher ischemia test values at 6 and 24 hours post PTCA for patients with AMI. The mean percent change from baseline and the mean value of the ischemia test are shown below. The following data

| % CHANGE FROM BASELINE | WITH AMI | | | WITHOUT AMI | | | T-TEST |
|---|---|---|---|---|---|---|---|
| | N | MEAN | SD | N | MEAN | SD | P |
| Immed Post PTCA | 19 | .083 | .137 | 41 | .101 | .111 | .0001 |
| 6 hrs Post PTCA | 15 | .091 | .137 | 39 | .027 | .153 | .2676 |
| 24 hrs Post PTCA | 14 | .130 | .158 | 27 | .019 | .081 | .2240 |

A side branch occlusion ("SBO") occurs when, as a result of balloon inflation, a side artery becomes obstructed, causing loss of blood flow and ischemia distal to the occlusion. Patients with side branch occlusion (SBO) were predicted to have more ischemia than those without. Patients were assigned to the SBO subset if their cardiologist indicated they had significant SBO.

Study results showed significantly higher ischemia test values immediately after and 6 hours after PTCA in patients with SBO. The following data includes patients in all study subsets. The number of patients varies because investigators were not always able to obtain blood samples at all four draw times.

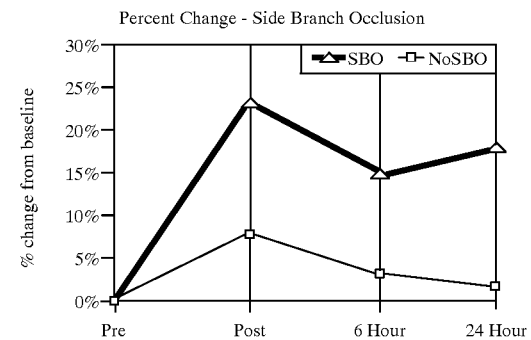

| % CHANGE FROM BASELINE | WITH SBO | | | WITHOUT SBO | | | T-TEST |
|---|---|---|---|---|---|---|---|
| | N | MEAN | SD | N | MEAN | SD | P |
| Immed Post PTCA | 8 | .228 | .144 | 51 | .076 | .102 | .0005 |
| 6 hrs Post PTCA | 8 | .150 | .156 | 45 | .033 | .149 | .0480 |
| 24 hrs Post PTCA | 8 | .168 | .222 | 33 | .013 | .098 | .1500 |

EXAMPLE 10
Assessment of the Patency of In-situ Coronary Stent

Coronary stents may be inserted during angioplasty and left in place on a permanent basis in order to hold open the artery and thus improve blood flow to the heart muscle and relieve angina symptoms. Stent insertion consists of the insertion of a wire mesh tube (a stent) to prop open an artery that has recently been cleared using angioplasty. The stent is collapsed to a small diameter, placed over an angioplasty balloon catheter and moved into the area of the blockage. When the balloon is inflated, the stent expands, locks in place and forms a rigid support to hold the artery open.

Stent use has increased significantly in just the past year, and is now used in the vast majority of patients, sometimes as an alternative to coronary artery bypass surgery. A stent may be used as an alternative or in combination with angioplasty. Certain features of the artery blockage make it suitable for using a stent, such as the size of the artery and location of the blockage. It is usually reserved for lesions that do not respond to angioplasty alone due to the reclosure of the expanded artery.

In certain selected patients, stents have been shown to reduce the renarrowing that occurs in 30–40 percent of patients following balloon angioplasty or other procedures using catheters. Stents are also useful to restore normal blood flow and keep an artery open if it has been torn or injured by the balloon catheter.

However, reclosure (referred to as restenosis) is a common problem with the stent procedure. In recent years doctors have used stents covered with drugs that interfere with changes in the blood vessel that encourage reclosure. These new stents have shown some promise for improving the long-term success of this procedure. Additionally, after a stent procedure has been done, patients are often placed on one or more blood thinning agents such as aspirin, Ticlopidine and/or Coumadin in order to prevent or prolong reclosure. Whereas aspirin may be used indefinitely; the other two drugs are used only for four to six weeks.

The present invention provides a mechanism for monitoring the functioning and patency of an in situ stent.

Stent patency was tested in the same study and same patient group in which post-myocardial infarction patients were studied (see Example 10). The study results showed significantly lower ischemia test values immediately after and 6 hours after PTCA for those patients with stents. The following data includes patients in the NonAMI subset only. The number of patients varies because investigators were not always able to obtain blood samples at all four draw times.

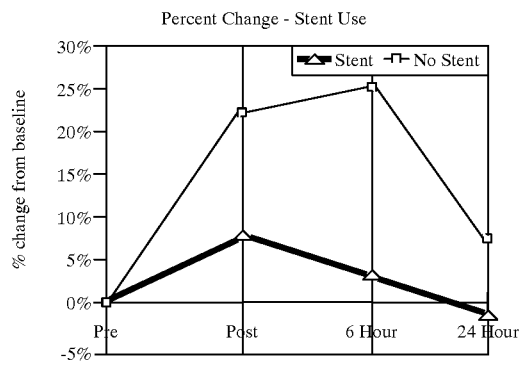

| % CHANGE FROM BASELINE | WITH STENT | | | WITHOUT STENT | | | T-TEST |
|---|---|---|---|---|---|---|---|
| | N | MEAN | SD | N | MEAN | SD | P |
| Immed Post PTCA | 37 | .089 | .105 | 4 | .210 | .117 | .0373 |
| 6 hrs Post PTCA | 36 | .009 | .139 | 3 | .243 | .153 | .0087 |
| 24 hrs Post PTCA | 26 | .022 | .080 | 1 | .071 | NA | NA |

EXAMPLE 11
Diagnosis and Assessment of Arrhythmic/Dysrhythmic Patients

The present invention provides a rapid method for assessing arrhythmias and diagnosing and measuring dsyrhythmias.

Rapid assessment and treatment of arrhythmias is key to a successful outcome: if treated in time, ventricular tachycardia and ventricular fibrillation can be converted into normal rhythm by administration of an electrical shock; alternatively, rapid heart beating can be controlled with medications which identify and destroy the focus of the rhythm disturbances. If an arrhythmia is not promptly diagnosed and treated, a stroke may be the likely result. Arrhythmia prevents the heart from fully pumping blood out of the heart chambers; the undisgorged blood remaining in the heart chamber will pool and clot. If a piece of the blood clot in the atria becomes lodged in an artery in the brain, a stroke results. About 15 percent of strokes occur in people with atrial fibrillation.

Traditionally, electrocardiography, also called ECG or EKG, is used to diagnosis the occurrence of an arrhythmia. (Also utilized are the "12 lead EKG" and signal-averaged electrocardiogram (S.A.E.C.G.), the S.A.E.C.G. to identify people who have the potential to experience a dangerous ventricular arrhythmia and the "12 lead EKG" primarily in people undergoing arrhythmias.) However, all of the electrocardiographic tests yield frequent false positive and false negative results. The present invention provides a method for supplementing all of the aforementioned electrocardiographic tests in order to reduce, if not avoid entirely, the frequency of false positive and false negative diagnoses.

Other diagnostics techniques typically used are invasive and thus possess greater risk. For instance, transesophageal echocardiography (T.E.E.) is an imaging procedure, in which a tube with a transducer on the end of it is passed down a person's throat and into the esophagus; images from TEE can give very clear pictures of the heart and its structures. Cardiac catheterization is another invasive procedure which allows for measurement and viewing of the pumping ability of the heart muscle, the heart valves and the coronary arteries. The shortcoming of these procedures, however, lies in their invasive nature.

The present invention provides a non-invasive method for diagnosis and measurement of dsyrhythmias which can be used in lieu of, or in supplementation of, the aforementioned invasive procedures.

Patients with dysrhythmias undergoing PTCA were predicted to have more ischemia than those without. (Dysrhythmia is cited in the medicl literature as a good indicator of ischemia.) In the 63 patient study detailed in Examples 10 and 11 patients were additionally assigned to a dysrhythmia subset if their medical record showed significant dysrhythmia during PTCA. Study results showed significantly higher ischemia test values immediately after and 6 hours after PTCA in patients with significant dysrhythmias. The following data includes patients in all study subsets. The number of patients varies because investigators were not always able to obtain blood samples at all four draw times.

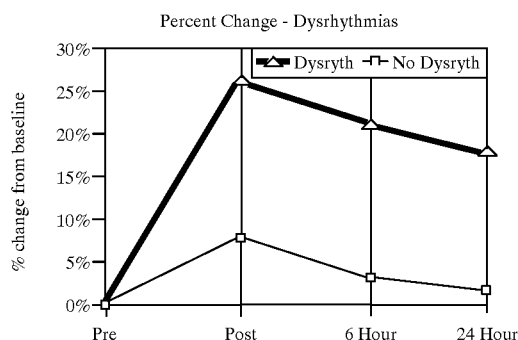

Percent Change - Dysrhythmias

| % CHANGE FROM BASELINE | WITH DYSRHYTHMIA | | | W/O DYSRHYTHMIA | | | T-TEST |
|---|---|---|---|---|---|---|---|
| | N | MEAN | SD | N | MEAN | SD | P |
| Immed Post PTCA | 5 | .265 | .151 | .57 | .079 | .103 | .0004 |
| 6 hrs Post PTCA | 5 | .204 | .175 | 51 | .035 | .141 | .0150 |
| 24 hrs Post PTCA | 5 | .144 | .236 | 37 | .017 | .107 | .3000 |

EXAMPLES 12–23

Use of N-terminus Peptide Probe in the Evaluation of Ischemia

Under the present invention, a four amino acid sequence found within the N-terminus sequence of albumin is the minimum sequence required for cobalt binding. This sequence has been identified as Asp-Ala-His-Lys (abbreviated "DAHK") (SEQ ID NO.1). The binding characteristics of this tetrapeptide have been extensively studied and it has been determined that this tetrapeptide may be used to detect the presence of ischemia.

Specifically, a biological sample containing albumin is contacted with $CoCl_2 \cdot 6H_2O$. Some of this cobalt will bind to albumin. The remaining free cobalt is then reacted with a known amount of D-A-H-K.R (SEQ ID NO.1) added to the biological sample, wherein R is any chemical group or enzyme, including no group at all or a fluorescent group, capable of being detected. Because D-A-H-K.R (SEQ ID NO.1) has a great affinity to cobalt (association constant $>10^6$) the free cobalt will attach to it. The D-A-H-K.R (SEQ ID NO.1) differs from Co-D-A-H-K.R (SEQ ID NO.1) spectroscopically. One distinction is that Co-D-A-H-K.R (SEQ ID NO.1) has an extinction coefficient that is 1.5 to 2 times the peptide alone. This phenomenon can be used to determine that the peptide bound cobalt (an increase in absorption at ~214 nm using HPLC or other methods).

EXAMPLE 12

To a 0.2 ml sample of blood or plasma is added 50 µL 0.1% $CoCl_2$. The mixture is incubated for 5 to 10 minutes. Thereafter, 50 µL of 1 mg/ml of D-A-H-K.R (SEQ ID NO.1) is added to the sample. (R can be a polymer or other substance having chemical and physical characteristics that will change when the cobalt binds to the peptide—causing a small current change or any other change that can be detected.) The sample is then centrifuged (Centricon 10 or 3) for 5 minutes, followed by HPLC analysis of the filtrate using a ultrahydrogel 120, 5µ column at 60° C.; isocratic run, mobile phase acetonitrile: ammonium acetate buffer 30 mM ph 8.0, 2:98; at 1 ml/minute and U.V. detection at 214 nm. Peptide peak appears at ~5.88 minutes.

The same procedure is run with peptide control (no cobalt). The difference in peak size between test (with cobalt) and control (no cobalt) is proportional to the amount of free cobalt and hence ischemia.

The following preliminary experiments illustrate the properties and critical characteristics of the peptide probe.

EXAMPLE 13

MEASUREMENT OF COBALT BINDING TO HSA AND OCTAPEPTIDE USING COLD COBALT BINDING ASSAY

OBJECTIVE: To investigate cobalt binding to the octapeptide and human serum albumin using cold cobalt binding assay.

EXPERIMENTAL: Octapeptide synthesized at the Inorganic Chemistry Department (BAM 1, Pat Ingrey, Cambridge): $NH_2$-Asp-Ala-His+-Lys+-Ser-Glu-Val-Ala-$CONH_2$ (SEQ ID NO.2) Molecular weight: 855.4 Da.

SOLUTIONS: $CoCl_2$ 0.1% (w/v)=4.2 mM; HSA 3% (w/v)(in 75 mM HEPES pH 7.4)=0.45 mM; Octapeptide 0.965 mM (in 75 mM HEPES pH 7.4); HEPES 75 mM pH 7.4; DTT 0. 15% (w/v); NaCl 0.85% (w/v)

METHOD: To two tubes each containing 200 μL of 75 mM HEPES pH 7.4 or 0.45 mM HSA in HEPES or 0.965 mM Peptide in HEPES add 50 μL $CoCl_2$ 0.1%; Allow to stand at room temperature for 10 minutes; Add 50 μL DTT 0.15% to one tube (test tube) and distilled $H_2O$ to the other (control tube); Keep for 2 minutes at room temperature; Add 1 ml NaCl 0.85%; Measure the absorbance at A470 nm of the test tube versus the blank

RESULTS:

| ID | A470 nm | | mean A470 | % bound |
|---|---|---|---|---|
| 75 mM HEPES Ph 7.4 | 1.087 | 1.083 | 1.085 | 0.0 |
| 0.45 mM HSA in HEPES pH 7.4 | 0.668 | 0.643 | 0.656 | 39.5 |
| 0.965 mM Peptide in HEPES pH 7.4 | 0.638 | 0.655 | 0.647 | 40.4 |

CONCLUSIONS: Under the conditions used for the binding measurements, this experiment shows that: 1. Cobalt binds to the "octapeptide" (N-Asp-Ala-His+-Lys+-Ser-Glu-Val-Ala, SEQ ID NO.1); 2. However the octapeptide (0.965 mM) binds cobalt with a stoichiometry of 1:2.3.

EXAMPLE 14

MASS SPECTROMETRY OF OCTAPEPTIDE AFTER THE ADDITION OF COBALT

OBJECTIVE: To investigate whether mass spectral study would provide molecular weight information for the octapeptide and its corresponding cobalt complex.

SOLUTIONS: Ammonium acetate 20 mM-pH 7.4 (with dilute ammonia solution); $CoCl_2$ 20 μM (in HPLC grade $H_2O$); Octapeptide 9.5 μM (in HPLC grade $H_2O$).

METHOD: 20 μM $CoCl_2$ (100 μl) was added to 9.5 μM octapeptide (100 μl) and mass spectrometry carried out.

RESULTS: The main molecular ion peak was observed at 855.4 Da, with minor peaks at 877.4 and 893.4 Da probably as a result of sodium and potassium cluster ions. After the addition of cobalt, an extra molecular ion peak was observed at 912.3 Da.

CONCLUSIONS: Octapeptide shows a molecular ion at 855 Da consistent with the expected molecular weight of the peptide moiety. Octapeptide plus cobalt complex shows a molecular ion at 912 Da suggesting that at least two protons are removed during the complex formation.

EXAMPLE 15

SPECTROPHOTOMETRIC ANALYSIS OF THE OCTAPEPTIDE AND OCTAPEPTIDE-COBALT COMPLEX

OBJECTIVE: It is clear from the previous mass spectrometry evidence that cobalt forms a complex with the octapeptide with a concomitant loss of two possible protons. Metal complexes in general show distinct absorption in the UV range and in many cases these complexes show either a hypsochromic or a bathochromic shift in the spectra. These shifts can be correlated to provide the energy of binding. It was therefore anticipated that the octapeptide-cobalt complexation would provide such information.

METHOD: The quartz cuvette contained 800 ul octapeptide+200 ul $H_2O$(control) or $CoCl_2$ (complex). Spectra were run from 180 to 800 nm on a single beam spectrophotometer.

CONCLUSIONS: Cobalt and octapeptide individually have peak absorbances at <200 and 225 nm respectively with little overlap. Following addition of a $CoCl_2$ solution to octapeptide (1.1:1) there was no significant shift in the k max (220 nm). The absorption band at this region broadened indicating complex formation, but the result could not be used to determine the binding energy (constant).

EXAMPLE 16

MASS SPECTROMETRY OF OCTAPEPTIDE AFTER THE ADDITION OF COBALT

OBJECTIVE: To investigate whether mass spectral study would provide molecular weight information for the peptide and its corresponding cobalt complex.

METHOD: 20 or 200 μM $CoCl_2$ (100 μl) was added to 22.9 μM octapeptide (100 μl) to give ratios of cobalt: octapeptide of 1:1.1 and 8.7:1 respectively. Mass spectra for the two samples were carried out as per conditions detailed in the previous experiment.

Figure 7:
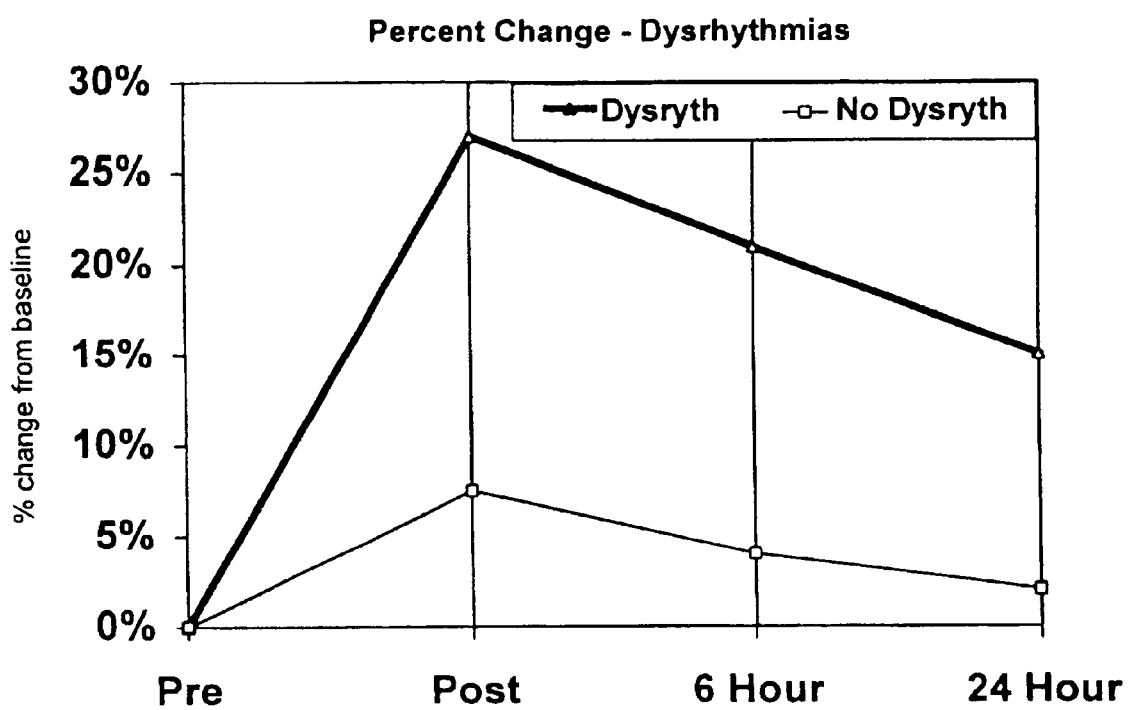
FIG. 7 is a chrt illustrating the percentage change from baseline in absorbance in patients that experience dysrhythmias during PTCA and in patiens that do not experience dysrhythmias during PTCA, as described in Example 12.

RESULTS: One major molecular ion peak was observed at 855.4 Da representing the octapeptide alone. After the addition of 20 μM cobalt to the octapeptide, two peaks were observed, a major peak at 855.3 representing octapeptide only plus a minor peak at 912.2 Da representing octapeptide-cobalt complex. Peak ratio of free octapeptide to octapeptide-cobalt complex was 1:0.15. A similar profile was observed following the addition of 200 μM cobalt to the octapeptide (FIG. 7). Peak ratio of free octapeptide to octapeptide-cobalt complex was 1:0.9.

CONCLUSIONS: On addition of cobalt (59 Da) to the octapeptide, the molecular ion peak should occur at 914 Da. The actual peak occurs at 912 Da, representing the loss of two protons. On addition of increasing concentrations of cobalt the peak ratio of free octapeptide to octapeptide-cobalt complex increased.

EXAMPLE 17

THE EFFECT OF OXYGEN ON THE BINDING CAPACITY OF OCTAPEPTIDE FOR COBALT

OBJECTIVE: Previous experiments have highlighted the requirement of oxygen in promoting cobalt binding to HSA. It may be anticipated that similar effects could be observed in the manner of cobalt binding to the octapeptide.

METHOD: Octapeptide-cobalt complex (no oxygen): HPLC grade $H_2O$ was bubbled with 100% helium for 10 minutes prior to use and used to prepare the above solutions. These were further deoxygenated for 10 minutes before adding 200 μM $CoCl_2$ (2 ml) to 22.9 μM octapeptide (2 ml). This mixture was again deoxygenated for 10 minutes prior to analysis by HPLC.

Octapeptide-cobalt complex (with oxygen) HPLC grade $H_2O$ was bubbled with 100% oxygen for 10 minutes prior to use and used to prepare the above solutions. These were further oxygenated for 10 minutes before adding 200 μM CoCl$_2$, (2 ml) to 22. μM octapeptide (2 ml). This mixture was again oxygenated for 10 minutes prior to analysis by HPLC.

HPLC Analysis: Chromatography was carried out on a KS437 styrene/DVB polymer column (4.6 mm×150 mm, pore diameter 100–150 A, BioDynamics) under isocratic conditions of 2% acetonitrile in 30 mM Ammonium acetate pH 8.0 at a flow rate of 2 ml/min. Peaks were detected at 230 nm. Chromatography gave two distinct peaks at 230 nm, the first peak representing octapeptide-cobalt complex and the second peak representing free octapeptide. Octapeptide-Co$^{2+}$ complex formed in the presence of oxygen gave a higher ratio of complex over free peptide, as indicated by the first peak being the larger of the two. Octapeptide-Co$^{2+}$ complex formed in the absence of oxygen again gives two peaks but the second peak is now the larger of the two, indicating less complex formation.

CONCLUSIONS: It would appear that oxygenated conditions enhance cobalt binding to the octapeptide.

EXAMPLE 18

THE EFFECT OF pH ON THE OCTAPEPTIDE

OBJECTIVE: To optimize chromatography conditions for analysis of octapeptide by HPLC.

METHOD: The octapeptide was analyzed by HPLC using a KS437 styrene/DVB Polymer column (4.6 mm×150 mm, pore diameter 100–150 A, 'BioDynamics) under isocratic conditions of 2% acetonitrile in 30 mM Ammonium acetate at pH 6.2, 7.5 and 8.0 at a flow rate of 2 ml/min. Peaks were detected at 230 nm.

RESULTS: At pH 6.2, the octapeptide eluted after 1.6 min. At pH 8.0 the retention time had increased to 2.1 min. When the octapeptide was run at pH 7.5, two peaks were observed at 1.6 and 2.1 min.

CONCLUSIONS: The octapeptide exists in two forms depending on pH. The protonated form elutes at pH 6.2, and the deprotonated form at pH 8.0.

EXAMPLE 19

THE EFFECT OF pH ON THE BINDING OF COBALT TO THE OCTAPEPTIDE.

OBJECTIVE: It was reported that the peptide peak 'shifted' when a solution of cobalt chloride was added to the octapeptide. It was decided to investigate this phenomenon fully as this would provide a direct tool for the determination of several parameters of cobalt binding to the octapeptide.

METHOD: 200 mM CoCl$_2$ (30 μl) was added to 2.3 mM octapeptide (270 μl), incubated at room temperature for 10 minutes and analyzed by HPLC. HPLC analysis: The octapeptide-cobalt complex was analyzed by HPLC using a KS437 styrene/DVB polymer column (4.6 mm×150 mm, pore diameter 100–150 A, BioDynamics) under isocratic conditions of 2% acetonitrile in 30 mM Ammonium acetate at pH 6.2 and 8.0 at a flow rate of 2 ml/min. Peaks were detected at 230 nm.

RESULTS: At pH 6.2, a single peak eluted after 1.6 min in the presence and absence of cobalt. At pH 8.0 however a single peak eluted after 1.2 min in the presence of cobalt and at 2.1 min in the absence of cobalt.

CONCLUSIONS: The octapeptide exists in two forms depending on pH. The protonated form that elutes at pH 6.2 is unable to bind cobalt and therefore its elution profile is unchanged. In contrast, the deprotonated form which exists at pH 8.0 is able to bind cobalt, resulting in an increased UV absorption and a decreased retention time, 1.2 min as opposed to 2.1 min for the free octapeptide.

EXAMPLE 20

TITRATION OF OCTAPEPTIDE WITH INCREASING CONCENTRATIONS OF COBALT

OBJECTIVE: To determine whether increasing concentrations of cobalt resulted in a corresponding increase in octapeptide-cobalt complex formation.

METHOD: Octapeptide was used at a final concentration of 2.1 mM throughout, with increasing concentrations of CoCl$_2$, as shown in the Table below:

| [CoCl$_2$] (mM) | Vol CoCl$_2$ added (μl) | [Octapeptide] (mM) | Vol octapeptide added (μl) | Ratio of octapeptide: CoCl$_2$ |
|---|---|---|---|---|
| 0 | 0 | 2.3 | 27 | 1:0 |
| 1 | 3 | 2.3 | 27 | 21:1 |
| 1.25 | 3 | 2.3 | 27 | 16.8:1 |
| 2.25 | 3 | 2.3 | 27 | 9.3:1 |
| 4.5 | 3 | 2.3 | 27 | 4.7:1 |
| 10 | 3 | 2.3 | 27 | 2.1:1 |
| 18 | 3 | 2.3 | 27 | 1.2:1 |
| 36 | 3 | 2.3 | 27 | 1:1.7 |
| 72 | 3 | 2.3 | 27 | 1:3.4 |
| 200 | 3 | 2.3 | 27 | 1:9.5 |

HPLC analysis: The octapeptide-cobalt complex was analyzed by HPLC using a KS437 styrene/DVB polymer column (4.6 mm×150 mm, pore diameter 100–150 A, BioDynamics) under isocratic conditions of 2% acetonitrile in 30 mM Ammonium acetate at pH 8.0 at a flow rate of 2 ml/min. Peaks were detected at 230 nm.

RESULTS: Mean % Peak Height:

| Final [CoCl$_2$] (mM) | Peak 1 (Octapeptide-Co complex) | Peak 2 (unknown) | Peak 3 (Octapeptide) |
|---|---|---|---|
| 0 | — | 3.72 | 96.28 |
| 0.1 | 7.44 | 7.08 | 85.49 |
| 0.125 | 9.79 | 7.55 | 82.66 |
| 0.225 | 15.65 | 15.66 | 68.52 |
| 0.45 | 25.36 | 19.67 | 54.98 |
| 1.0 | 58.66 | — | 50.42 |
| 1.8 | 61.19 | 14.97 | 23.85 |
| 3.6 | 69.55 | 13.69 | 16.76 |
| 7.2 | 71.49 | 14.47 | 14.05 |
| 20.0 | 82.17 | 10.27 | 7.56 |

From the table immediately proceeding, a plot of Log cobalt concentration versus % peak height for peak 3 was produced using Prism software. The 50% binding constant as deduced from the exponential graph had a value of 0.6461 mM.

CONCLUSIONS: For 50% binding, 0.6461 mM Co$^{2+}$ binds to 2.1 mM octapeptide. Therefore for 100% binding, 1.2922 mM Co$^{2+}$ binds to 2.1 mM octapeptide. The stoichiometry of cobalt binding to octapeptide is 0.615 cobalt to 1 octapeptide.

EXAMPLE 21

LIQUID CHROMATOGRAPHY-MASS SPECTROMETRY OF OCTAPEPTIDE AFTER THE ADDITION OF COBALT

OBJECTIVE: To investigate whether mass spectral study would provide molecular weight information for the peptide and its corresponding cobalt complex.

METHOD: 200 mM $CoCl_2$ or $H_2O$ (3 μl) was added to 2.3 mM octapeptide (27 μl) and incubated at room temperature for 10 minutes. LC-MS analysis: Liquid chromatography was performed using a KS437 styrene/DVB polymer column (4.6 mm×150 mm, pore diameter 100–150 A, BioDynamics) under isocratic conditions of 2% acetonitrile in 30 mM Ammonium acetate at pH 8.0 at a flow rate of 0.5 ml/min. Peaks were detected at 230 nm, and analyzed by on line mass spectrometry.

RESULTS: In the control sample, two molecular ion peaks were observed at 855.2 Da, representing the octapeptide alone, and at 877.2 Da, representing an octapeptide-sodium cluster. After the addition of 200 mM cobalt, one major peak was observed at 911.1 Da.

CONCLUSIONS: On addition of cobalt (59 Da) to the octapeptide, the molecular ion peak should occur at 914 Da. The actual peak occurs at 911 Da, representing the loss of protons

EXAMPLE 22

ENDOPROTEASE LYS-C DIGEST OF OCTAPEPTIDE AND ITS SUBSEQUENT INCUBATION WITH COBALT.

OBJECTIVE: Previous experiments confirm that $CoCl_2$ forms a stable complex with the octapeptide. In order to elucidate the site of attachment, the octapeptide was cleaved stereoselectively with the endoprotease Lys-C. The resultant tetrapeptides upon incubation with $CoCl_2$ would allow elucidation of the probable binding site.

METHOD: Octapeptide 1.97 mg/ml (250 p1) was incubated with the endoprotease Lys-C100 μg/ml (50 μl) at a substrate: enzyme ratio of 100:1 (w/w) in 8.3 mM Tricine, 1.6 mM EDTA pH 8.0 at 37° C. for 24 h. After digestion, 27 μl of the product was incubated with 200 mM $CoCl_2$ (3 μl) at 20° C. for 10 minutes prior to analysis by HPLC. HPLC Analysis: The products from the Lys-C digest were analyzed by HPLC using an amino column (4.6 mm×250 mm, pore diameter 100 Å, BioDynamics-73) under isocratic conditions of 30 mM Ammonium acetate at pH 8.0 at a flow rate of 1.5 ml/min. Peaks were detected at 230 nm.

RESULTS: When the digested Lys-C products were run on HPLC, two peaks were observed at 2.6 and 8.9 min, designated tetrapeptides 1 and 2 respectively. Similarly after addition of cobalt to the digested products two peaks were again observed. However, tetrapeptide 1 exhibited an increased UV absorption and decreased retention time, eluting at 1.7 min as opposed to 2.6 min.

CONCLUSIONS: The octapeptide was digested at the C terminus of the lysine residue by the endoprotease yielding two tetrapeptides. On addition of cobalt to the endoprotease digested octapeptide, a single tetrapeptide-cobalt complex was formed with tetrapeptide 1. There appeared to be no effect on tetrapeptide 2.

EXAMPLE 23

MASS SPECTROMETRY ANALYSIS OF THE TETRAPEPTIDE 1—COBALT COMPLEX.

OBJECTIVE: To determine the identity of tetrapeptide 1.

EXPERIMENTAL: Tetrapeptides 1 and 2 were fractionated by HPLC and collected (experiment 59). $CoCl_2$ 1.2 mM (3 μl) was added to tetrapeptide 1 (27 μl) and incubated at room temperature for 10 minutes. Samples were subsequently run on MS as described previously.

RESULTS: Tetrapeptide 1 gave two molecular ion peaks at 470.1 and 477.1 Da. Tetrapeptide 2 gave a single peak at 404.0 Da. Tetrapeptide 1-cobalt complex gave two peaks at 477.1 and 526 Da.

CONCLUSIONS: Tetrapeptide 1 is determined to be Asp-Ala-His-Lys (SEQ ID NO.1) with a molecular weight of 469 Da. Tetrapeptide 2 is determined to be Ser-Glu-Val-Ala (404 Da) (SEQ ID NO.3). Cobalt binds to Asp-Ala-His-Lys (SEQ ID NO.1) forming a complex of 526 Da with a loss of 3 protons. The molecular ion peak observed at 477.1 Da is a contaminant from the Lys-C preparation.

The above description of the invention, including Examples 1 through 24, is intended to be illustrative and not limiting. Various changes or modification in the embodiments described may occur to those skilled in the art. These can be made without departing from the spirit or scope of the invention.

We claim:

1. A method for detecting the occurrence or non-occurrence of an ischemic event in a patient comprising the steps of:
   (a) contacting a biological sample containing albumin from said patient with an excess quantity of a metal ion salt, whereby said metal ion binds to the N-terminus of naturally occurring human albumin, to form a mixture containing bound metal ions and unbound metal ions,
   (b) determining the amount of metal ions bound to the albumin N-terminus, and
   (c) correlating the amount of bound metal ions to a known value to determine the occurrence or non-occurrence of an ischemic event.

2. The method of claim 1, wherein said sample is serum or plasma.

3. The method of claim 1, wherein said sample is purified albumin.

4. The method of claim 1, wherein said metal ion salt is a salt of a transition metal ion of Groups 1b–7b or 8 of the Periodic Table of the elements.

5. The method of claim 1, wherein said metal ion salt is a salt of a metal selected from the group consisting of V, As, Co, Sb, Cr, Mo, Mn, Ba, Zn, Ni, Hg, Cd, Fe, Pb, Au and Ag.

6. The method of claim 1, wherein said metal ion is cobalt.

7. The method of claim 1, wherein step (b) is conducted using atomic absorption or atomic emission spectroscopy.

8. The method of claim 1, wherein step (b) is conducted using an immunological assay.

9. A method for ruling-out the existence of ischemia in a patient, comprising the method of claim 1, wherein said patient possesses one or more cardiac risk factors, said cardiac risk factors being selected from the group consisting of: age between 35 to 50 years, history of smoking, diabetes mellitus, obesity, high blood pressure, high cholesterol, elevated low density lipoproteins and strong family history of cardiac disease.

10. A method for ruling-out the occurrence of a temporally-limited ischemic event in a patient comprising the method of claim 1.

11. A method of detecting the existence of ischemia in an asymptomatic patient comprising the method of claim 1.

12. A method for the evaluation of patients suffering from stroke-like signs to determine the occurrence or non-occurrence of a stroke, comprising the method of claim 1.

13. A method for distinguishing between the occurrence of an ischemic stroke and a hemorrhagic stroke, comprising the method of claim 1.

14. A method for assessing the efficacy of an angioplasty procedure, comprising the method of claim 1.

15. A method for assessing the efficacy of thrombolytic drug therapy, comprising the method of claim 1.

16. A method for detecting in a pregnant woman the occurrence of placental insufficiency, comprising application of the method of claim 1.

17. The method of claim 8, wherein said immunological assay is conducted using an antibody specific to an antigen comprising the compound Asp-Ala-His-Lys-R, wherein R is said metal ion.

18. The method of claim 17, wherein said antibody possesses known fluorescent properties.

19. The method of claim 8, wherein said immunological assay is conducted using an antibody to human serum albumin.

* * * * *

UNITED STATES PATENT AND TRADEMARK OFFICE
CERTIFICATE OF CORRECTION

PATENT NO. : 6,492,179 B1
DATED : December 10, 2002
INVENTOR(S) : Bar-Or et al.

It is certified that error appears in the above-identified patent and that said Letters Patent is hereby corrected as shown below:

<u>Title page,</u>
Item [*] Notice, should read:
-- [*] Notice: This patent issued on a continued prosecution application filed under CFR 1.53(d), and is subject to the twenty year patent term provisions of 35 U.S.C. 154 (a) "0" day. --

Signed and Sealed this

Twenty-eighth Day of October, 2003

JAMES E. ROGAN
*Director of the United States Patent and Trademark Office*